US012471949B2

(12) United States Patent
Anderson

(10) Patent No.: US 12,471,949 B2
(45) Date of Patent: Nov. 18, 2025

(54) REINFORCED MEDICAL BALLOON

(71) Applicant: BOSTON SCIENTIFIC SCIMED, INC., Maple Grove, MN (US)

(72) Inventor: James M. Anderson, Corcoran, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 276 days.

(21) Appl. No.: 18/197,211

(22) Filed: May 15, 2023

(65) Prior Publication Data

US 2023/0363786 A1 Nov. 16, 2023

Related U.S. Application Data

(60) Provisional application No. 63/342,222, filed on May 16, 2022.

(51) Int. Cl.

| | |
|---|---|
| ***A61B 17/3207*** | (2006.01) |
| *A61B 17/00* | (2006.01) |
| *A61M 25/10* | (2013.01) |

(52) U.S. Cl.

CPC ................ *A61B 17/320725* (2013.01); *A61B 2017/00243* (2013.01); *A61B 2017/00783* (2013.01); *A61M 2025/1059* (2013.01)

(58) Field of Classification Search

CPC ...... A61B 17/320725; A61B 17/32075; A61B 2017/00243; A61B 2017/00783; A61M 2025/1059

See application file for complete search history.

(56) References Cited

U.S. PATENT DOCUMENTS

| | | |
|---|---|---|
| 5,196,024 A | 3/1993 | Barath |
| 5,209,749 A | 5/1993 | Buelna |
| 5,226,887 A | 7/1993 | Farr et al. |

(Continued)

FOREIGN PATENT DOCUMENTS

| | | |
|---|---|---|
| DE | 3402573 A1 | 8/1985 |
| EP | 1453414 A2 | 9/2004 |

(Continued)

OTHER PUBLICATIONS

International Search Report and Written Opinion dated Oct. 5, 2023 for International Application No. PCT/US2023/022216.

*Primary Examiner* — Tuan V Nguyen

(74) *Attorney, Agent, or Firm* — Seager, Tufte & Wickhem LLP

(57) ABSTRACT

Example medical devices are disclosed. An example medical device includes an elongate shaft having a distal end region and a balloon coupled to the distal end region, the balloon including a wall, a distal waist, a proximal waist and body portion positioned between the distal waist and the proximal waist. The medical device also includes a first reinforced region positioned along the body portion, the first reinforced region including a first plurality of filaments and a second reinforced region positioned along the body portion, the second reinforced region including a second plurality of filaments. Further, the first reinforced region is circumferentially spaced from the second reinforced region such that the balloon wall extending between the first and the second reinforced regions is devoid of a filament.

17 Claims, 15 Drawing Sheets

(56) References Cited

U.S. PATENT DOCUMENTS

| | | | |
|---|---|---|---|
| 5,320,634 | A | 6/1994 | Vigil et al. |
| 5,456,666 | A | 10/1995 | Campbell et al. |
| 5,458,572 | A | 10/1995 | Campbell et al. |
| 5,616,149 | A | 4/1997 | Barath |
| 5,628,746 | A | 5/1997 | Clayman |
| 5,649,941 | A | 7/1997 | Lary |
| 5,713,913 | A | 2/1998 | Lary et al. |
| 5,718,684 | A | 2/1998 | Gupta |
| 5,797,935 | A | 8/1998 | Barath |
| 6,425,882 | B1 | 7/2002 | Vigil |
| 6,500,186 | B2 | 12/2002 | Lafontaine et al. |
| 6,562,062 | B2 | 5/2003 | Jenusaitis et al. |
| 6,632,231 | B2 | 10/2003 | Radisch |
| 6,746,463 | B1 | 6/2004 | Schwartz |
| 6,808,531 | B2 | 10/2004 | Lafontaine et al. |
| 6,951,566 | B2 | 10/2005 | Lary |
| 7,011,670 | B2 | 3/2006 | Radisch, Jr. |
| 7,029,483 | B2 | 4/2006 | Schwartz |
| 7,153,315 | B2 | 12/2006 | Miller |
| 7,172,609 | B2 | 2/2007 | Radisch, Jr. |
| 7,279,002 | B2 | 10/2007 | Shaw et al. |
| 7,291,158 | B2 | 11/2007 | Crow et al. |
| 7,303,572 | B2 | 12/2007 | Melsheimer et al. |
| 7,329,267 | B2 | 2/2008 | Weber |
| 7,338,463 | B2 | 3/2008 | Vigil |
| 7,396,358 | B2 | 7/2008 | Appling et al. |
| 7,413,558 | B2 | 8/2008 | Kelley et al. |
| 7,494,497 | B2 | 2/2009 | Weber |
| 7,566,319 | B2 | 7/2009 | Mcauley et al. |
| 7,632,288 | B2 | 12/2009 | Wu |
| 7,658,744 | B2 | 2/2010 | Jackson |
| 7,691,116 | B2 | 4/2010 | Goodin et al. |
| 7,754,047 | B2 | 7/2010 | Kelley |
| 7,758,604 | B2 | 7/2010 | Wu et al. |
| 7,879,053 | B2 | 2/2011 | Trinidad |
| 7,887,557 | B2 | 2/2011 | Kelley et al. |
| 7,951,111 | B2 | 5/2011 | Drasler et al. |
| 7,993,358 | B2 | 8/2011 | O'Brien |
| 8,038,691 | B2 | 10/2011 | Bence et al. |
| 8,323,243 | B2 | 12/2012 | Schneider et al. |
| 8,323,307 | B2 | 12/2012 | Hardert |
| 8,361,096 | B2 | 1/2013 | Bence et al. |
| 8,454,637 | B2 | 6/2013 | Aggerholm et al. |
| 8,690,824 | B2 | 4/2014 | Holman et al. |
| 8,690,903 | B2 | 4/2014 | Bence et al. |
| 8,858,855 | B2 | 10/2014 | Horn et al. |
| 8,870,816 | B2 | 10/2014 | Chambers et al. |
| 8,876,882 | B2 | 11/2014 | Barongan |
| 8,900,215 | B2 | 12/2014 | Pepper et al. |
| 8,906,049 | B2 | 12/2014 | Chambers |
| 8,945,047 | B2 | 2/2015 | Mcauley et al. |
| 8,986,248 | B2 | 3/2015 | Kunis |
| 8,992,553 | B2 | 3/2015 | Diamant et al. |
| 9,017,353 | B2 | 4/2015 | Bence et al. |
| 9,066,749 | B2 | 6/2015 | Burton et al. |
| 9,095,688 | B2 | 8/2015 | Burton |
| 9,119,944 | B2 | 9/2015 | Chambers et al. |
| 9,179,936 | B2 | 11/2015 | Feld et al. |
| 9,192,747 | B2 | 11/2015 | Hardert |
| 9,199,066 | B2 | 12/2015 | Konstantino et al. |
| 9,211,394 | B2 | 12/2015 | Leffel |
| 9,216,033 | B2 | 12/2015 | Feld et al. |
| 9,226,768 | B2 | 1/2016 | Gunderson et al. |
| 9,242,081 | B2 | 1/2016 | Drasler et al. |
| 9,254,145 | B2 | 2/2016 | Teeslink et al. |
| 9,302,071 | B2 | 4/2016 | Manderfeld et al. |
| 9,302,079 | B2 | 4/2016 | Burton et al. |
| 9,320,530 | B2 | 4/2016 | Grace |
| 9,327,102 | B2 | 5/2016 | Aggerholm et al. |
| 9,339,291 | B2 | 5/2016 | Aggerholm et al. |
| 9,351,756 | B2 | 5/2016 | Gershony et al. |
| 9,364,254 | B2 | 6/2016 | Gershony et al. |
| 9,364,255 | B2 | 6/2016 | Weber |
| 9,375,328 | B2 | 6/2016 | Farnan |
| 9,375,555 | B2 | 6/2016 | Pedersen et al. |
| 10,463,519 | B2 | 11/2019 | Aggerholm et al. |
| 11,154,320 | B2 | 10/2021 | Haverkost et al. |
| 2002/0010489 | A1 | 1/2002 | Grayzel et al. |
| 2002/0151918 | A1 | 10/2002 | Lafontaine et al. |
| 2003/0032973 | A1 | 2/2003 | Jenusaitis et al. |
| 2003/0040770 | A1 | 2/2003 | Radisch, Jr. |
| 2003/0078606 | A1 | 4/2003 | Lafontaine et al. |
| 2003/0144677 | A1 | 7/2003 | Lary |
| 2003/0163148 | A1 | 8/2003 | Wang et al. |
| 2003/0229370 | A1 | 12/2003 | Miller |
| 2004/0034384 | A1 | 2/2004 | Fukaya |
| 2004/0098018 | A1 | 5/2004 | Radisch, Jr. |
| 2004/0122457 | A1 | 6/2004 | Weber |
| 2004/0127792 | A1 | 7/2004 | Siejko et al. |
| 2004/0127920 | A1 | 7/2004 | Radisch, Jr. |
| 2004/0133223 | A1 | 7/2004 | Weber |
| 2004/0199191 | A1 | 10/2004 | Schwartz |
| 2004/0230178 | A1 | 11/2004 | Wu |
| 2004/0243156 | A1 | 12/2004 | Wu et al. |
| 2005/0038383 | A1 | 2/2005 | Kelley et al. |
| 2005/0070888 | A1 | 3/2005 | Dimatteo et al. |
| 2005/0119678 | A1 | 6/2005 | O'Brien et al. |
| 2005/0137615 | A1 | 6/2005 | Mapes et al. |
| 2005/0137616 | A1 | 6/2005 | Vigil |
| 2005/0137617 | A1 | 6/2005 | Kelley et al. |
| 2005/0149102 | A1 | 7/2005 | Radisch et al. |
| 2005/0228343 | A1 | 10/2005 | Kelley |
| 2005/0240148 | A1 | 10/2005 | Cheves et al. |
| 2005/0240212 | A1 | 10/2005 | Mcauley et al. |
| 2005/0251198 | A1 | 11/2005 | Smith et al. |
| 2005/0261721 | A1 | 11/2005 | Radisch et al. |
| 2005/0288629 | A1 | 12/2005 | Kunis |
| 2006/0106412 | A1 | 5/2006 | Crow et al. |
| 2006/0106413 | A1 | 5/2006 | Bence et al. |
| 2006/0111736 | A1 | 5/2006 | Kelley |
| 2006/0116700 | A1 | 6/2006 | Crow |
| 2006/0116701 | A1 | 6/2006 | Crow |
| 2006/0129093 | A1* | 6/2006 | Jackson ......... A61B 17/320725 604/96.01 |
| 2006/0135980 | A1 | 6/2006 | Trinidad |
| 2006/0184191 | A1 | 8/2006 | O'Brien |
| 2006/0247674 | A1 | 11/2006 | Roman |
| 2007/0016232 | A1 | 1/2007 | St. Martin et al. |
| 2007/0060863 | A1 | 3/2007 | Goeken et al. |
| 2007/0213752 | A1 | 9/2007 | Goodin et al. |
| 2009/0192537 | A1 | 7/2009 | O'Brien |
| 2009/0240270 | A1 | 9/2009 | Schneider et al. |
| 2009/0281490 | A1 | 11/2009 | Mcauley et al. |
| 2013/0116655 | A1* | 5/2013 | Bacino .............. A61M 25/1002 604/509 |
| 2016/0136397 | A1 | 5/2016 | Konstantino et al. |
| 2020/0114130 | A1* | 4/2020 | Davies, Jr. ............ A61M 25/10 |
| 2020/0230375 | A1 | 7/2020 | Hall et al. |
| 2021/0153891 | A1 | 5/2021 | Madej et al. |

FOREIGN PATENT DOCUMENTS

| | | | |
|---|---|---|---|
| WO | 03049603 | A2 | 6/2003 |
| WO | 03049603 | A3 | 10/2003 |

* cited by examiner

REINFORCED MEDICAL BALLOON

CROSS-REFERENCE TO RELATED APPLICATIONS

This application claims the benefit of U.S. Prov. Pat. App. No. 63/342,222, filed May 16, 2022, titled REINFORCED MEDICAL BALLOON, which is incorporated herein by reference.

TECHNICAL FIELD

The present disclosure relates to methods and apparatus for performing valvuloplasty. More particularly, the present disclosure relates to methods and apparatus for performing valvuloplasty using reinforced valvuloplasty balloons and reinforced valvuloplasty balloons that include one or more cutting members coupled to the valvuloplasty balloon.

BACKGROUND

Heart valve stenosis or calcification is a common manifestation in valvular heart disease, and may often be a leading indicator for balloon valvuloplasty and/or valve replacement therapy. In some instances, balloon valvuloplasty may be beneficial in improving the lifestyle of patients suffering from valve stenosis and may also contribute to a successful valve replacement procedure.

Stenotic or narrowed heart valves may be treated with a number of relatively non-invasive medical procedures including percutaneous transluminal balloon valvuloplasty (PTBV), percutaneous transcatheter heart valve replacement (PTVR), atherectomy and combinations thereof. Valvuloplasty techniques typically involve the use of a balloon catheter which is advanced over a guidewire such that a valvuloplasty balloon is positioned adjacent a stenotic heart valve. Once positioned in the proper location within the heart valve, the balloon is then inflated and the narrowed heart valve is expanded.

In some instances, balloon valvuloplasty may be insufficient to treat a severely diseased heart valve. In such cases, percutaneous transcatheter heart valve replacement (PTVR) may be performed to replace the native heart valve with an artificial heart valve. One method of performing percutaneous transcatheter heart valve replacement may include the use of a valvuloplasty balloon equipped with one or more cutting members to score the stenotic heart valve and thus prepare the native valve tissue for implantation of a replacement heart valve. Thus, valvuloplasty balloons equipped with cutting members have been developed to attempt to enhance heart valve replacement treatments. There is an ongoing need for improved valvuloplasty balloons, including cutting valvuloplasty balloons, and improved methods of treating valvular heart disease.

BRIEF SUMMARY

This disclosure provides design, material, manufacturing method, and use alternatives for medical devices. An example medical device includes an elongate shaft having a distal end region and a balloon coupled to the distal end region, the balloon including a wall, a distal waist, a proximal waist and body portion positioned between the distal waist and the proximal waist. The medical device also includes a first reinforced region positioned along the body portion, the first reinforced region including a first plurality of filaments and a second reinforced region positioned along the body portion, the second reinforced region including a second plurality of filaments. Further, the first reinforced region is circumferentially spaced from the second reinforced region such that the balloon wall extending between the first and the second reinforced regions is devoid of a filament.

Alternatively or additionally to any of the embodiments above, wherein the balloon wall extending between the first and second reinforced regions includes a first elasticity and wherein the first and the second reinforced regions include a second elasticity less than the first elasticity.

Alternatively or additionally to any of the embodiments above, wherein the balloon is configured to be inflated to a first pressure, and wherein the balloon wall devoid of a filament has a diameter at the first pressure and wherein the first reinforced region has a diameter at the first pressure, and wherein the diameter of the balloon wall devoid of a filament is greater than the diameter of the first reinforced region at the first pressure.

Alternatively or additionally to any of the embodiments above, wherein the first plurality of filaments are arranged in a braided configuration, and wherein the second plurality of filaments are arranged in a braided configuration.

Alternatively or additionally to any of the embodiments above, wherein each of the first plurality of filaments and the second plurality of filaments include a wire.

Alternatively or additionally to any of the embodiments above, wherein each of the first plurality of filaments and the second plurality of filaments include a fiber.

Alternatively or additionally to any of the embodiments above, wherein the first plurality of filaments are arranged into a first strip of braided filaments extending along the body portion, and wherein the second plurality of filaments are arranged into a second strip of braided filaments extending along the body portion.

Alternatively or additionally to any of the embodiments above, wherein the first reinforced region includes a reinforced assembly, the reinforced assembly including a base material, a plurality of filaments attached to the base material and a polymer coating attached to the plurality of filaments, wherein the reinforced assembly is configured to be separately attached to an outer surface of the body.

Alternatively or additionally to any of the embodiments above, wherein the balloon wall includes an inner layer have a first durometer and an outer layer having a second durometer greater than the first durometer.

Alternatively or additionally to any of the embodiments above, wherein the first reinforced region further includes a polymer coating disposed along the first plurality of filaments.

Alternatively or additionally to any of the embodiments above, wherein the first reinforced region further includes a cutting member attached thereto.

Alternatively or additionally to any of the embodiments above, wherein the cutting member includes a wire having a first region and a second region, and wherein the first region is configured to be attached to the plurality of filaments, and wherein the second region is configured to extend radially away from the first region.

Alternatively or additionally to any of the embodiments above, wherein one or more of the plurality of filaments engage a portion of the first region of the wire.

Alternatively or additionally to any of the embodiments above, wherein the cutting member includes an atherotome.

An example balloon catheter includes an elongate shaft having a distal end region and a balloon coupled to the distal end region, the balloon including a wall and a plurality of reinforced regions extending longitudinally along a cylindrical body portion of the balloon. Further, each of the plurality of reinforced regions includes a mesh material. Additionally, each of the plurality of reinforced regions is circumferentially spaced away from one another such that the portion of the balloon wall positioned between any two reinforced regions is devoid of a filament.

Alternatively or additionally to any of the embodiments above, wherein the portion of the balloon wall extending between any two reinforced regions includes a first elasticity and wherein each of the plurality of reinforced regions includes a second elasticity less than the first elasticity.

Alternatively or additionally to any of the embodiments above, wherein the mesh material includes a plurality of wires.

Alternatively or additionally to any of the embodiments above, wherein the mesh material includes a plurality of fibers.

Alternatively or additionally to any of the embodiments above, wherein at least one of the plurality of reinforced regions further includes a cutting member attached thereto.

An example method of using a balloon catheter includes providing a balloon catheter. The balloon catheter includes a balloon coupled to the distal end region, the balloon including a cylindrical body portion, a first reinforced region positioned along the body portion, the first reinforced region including a first plurality of filaments and a second reinforced region positioned along the body portion, the second reinforced region including a second plurality of filaments. Additionally, the first reinforced region is circumferentially spaced from the second reinforced region such that the balloon wall extending between the first and the second reinforced regions is devoid of a filament. The method further includes advancing the balloon catheter to a target site, inflating the balloon, whereby the balloon engages target site, deflating the balloon and withdrawing the balloon catheter from the blood vessel.

The above summary of some embodiments is not intended to describe each disclosed embodiment or every implementation of the present disclosure. The Figures and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

DETAILED DESCRIPTION

Figure 1:
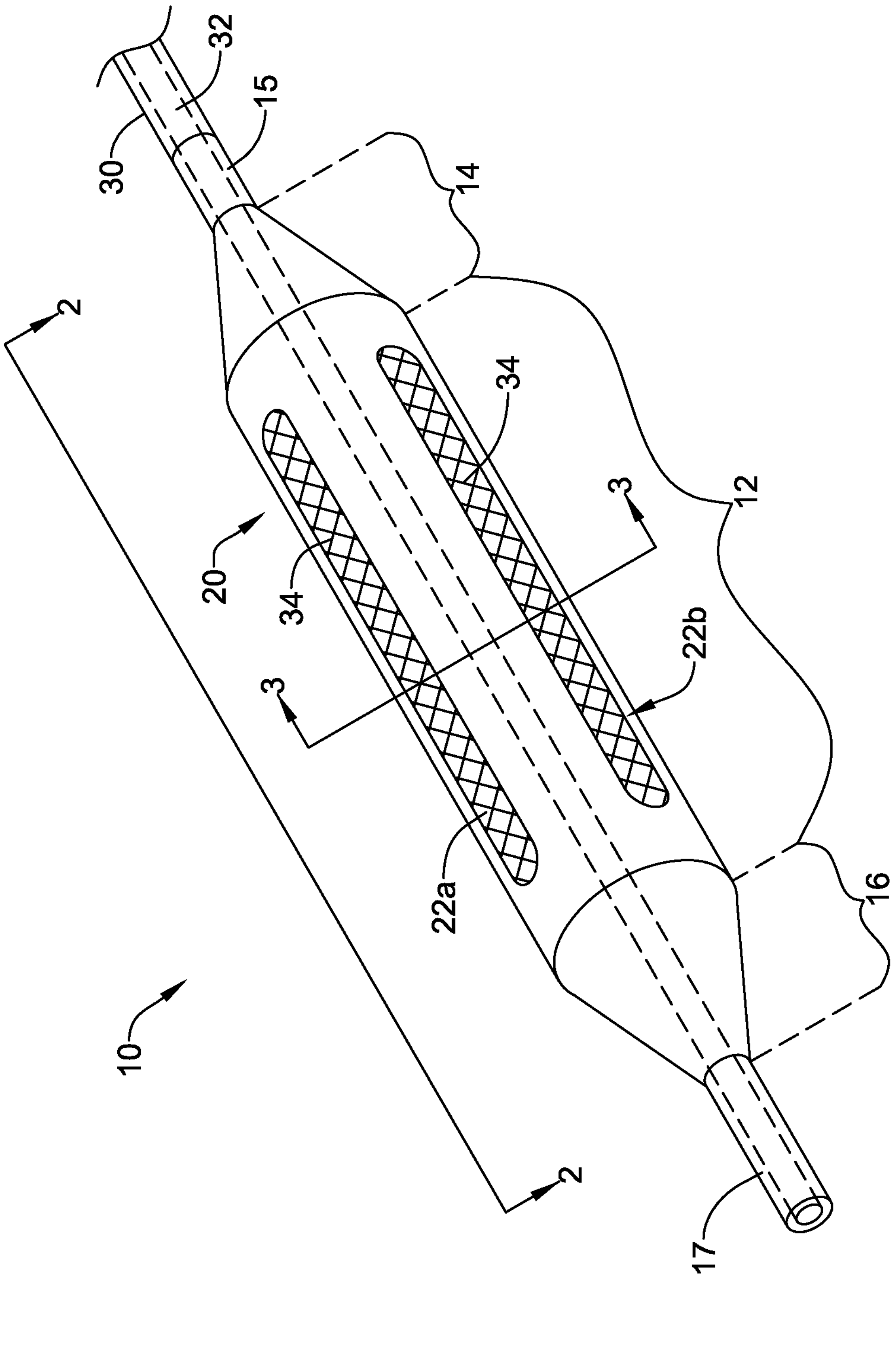
FIG. 1 illustrates a perspective view of an example medical balloon.

The following description should be read with reference to the drawings wherein like reference numerals indicate like elements throughout the several views. The detailed description and drawings illustrate example embodiments of the claimed disclosure.

As discussed above, medical balloons may be utilized in a variety of medical treatments. For example, in a valvuloplasty procedure, a valvuloplasty balloon may be used to expand a diseased heart valve. A cutting balloon may also be used to prepare (e.g., score) a stenotic heart valve for implantation of a replacement heart valve.

Valvuloplasty balloons may be delivered to a target site by advancing a balloon catheter over a guidewire to the target site. In some cases, the pathway to a target site may be tortuous and/or narrow. Upon reaching the site, the valvuloplasty balloon may be expanded by injecting a fluid into the interior of the balloon. Expanding the valvuloplasty balloon may radially expand the stenotic heart valve such that normal blood flow may be restored through the valve.

In some instances, it may be desirable to utilize high pressure valvuloplasty balloons when treating a particular target site (e.g., a stenotic heart valve). To achieve the desired pressure or force against tissue at the target site, a valvuloplasty balloon may be constructed with a thicker balloon wall. However, the thicker balloon wall may increase the profile (e.g., outer diameter) of the balloon when in a deflated configuration. Minimizing the profile of the balloon in a deflated configuration is important as the profile effects the ease and ability of the valvuloplasty balloon to pass through a guide catheter through the coronary arteries and across a narrowed heart valve. To minimize the outer diameter of the balloon in its deflated condition, it may be desirable to control the folding/refolding mechanics of the valvuloplasty balloon. Examples disclosed herein may include valvuloplasty balloons including reinforced segments designed to control the folding mechanics of the balloon while also providing an anchoring component for attachment of one or more cutting members.

FIG. 1 illustrates an example balloon catheter 10. The balloon catheter 10 may include an expandable medical balloon 20 mounted to a distal end of an outer catheter shaft 30. The medical balloon 20 may be designed to be utilized in a variety of medical procedures, including a valvuloplasty procedure. The catheter shaft 30 may extend from a manifold assembly (not shown) positioned at a proximal end of the catheter shaft 30. The balloon 20 may further include a body portion 12, a proximal cone portion 14, a distal cone portion 16, a proximal waist portion 15, and a distal waist portion 17. The body portion 12 may be positioned between the proximal cone portion 14 and the distal cone portion 16, with the proximal waist portion 15 extending proximal of the proximal cone portion 14 and the distal waist portion 17 extending distal of the distal cone portion 16. The balloon 20 may be secured to the outer catheter shaft 30 at the proximal waist 15. It can be appreciated that an inner shaft 32 may extend within the outer catheter shaft 30, through an inner cavity of the balloon 20 and be secured to the distal waist 17.

The inner shaft 32 may include an inner lumen. In at least some embodiments, the inner lumen of the inner shaft 32 may be a guidewire lumen. Accordingly, the catheter 10 may be advanced over guidewire to the desired location. The guidewire lumen may extend along essentially the entire length of the catheter shaft 30 such that the catheter 10 resembles a traditional "over-the-wire" catheter. Alternatively, the guidewire lumen may extend along only a portion of the shaft 30 so that the catheter 10 resembles a "single-operator-exchange" catheter.

Further, the outer shaft 30 may also include an inflation lumen that may be used, for example, to transport inflation media to and from balloon 20. When the outer shaft 30 is disposed over inner shaft 32, the inflation lumen may be defined within the space between the outer surface of the inner shaft 32 and the inner surface of the outer shaft 30.

As will be discussed in detail below, the balloon 20 may include a balloon wall constructed of one or more layers, wherein each of the layers may be constructed from different balloon materials. For example, the balloon wall 24 (shown in the detailed view of FIG. 3) of the balloon 20 may include an inner layer and an outer layer, whereby the inner layer is constructed of a lower durometer (e.g., softer) material as compared to the outer layer. This two-layer construction may be referred to as a bi-layer balloon base layer. Further, the inner and outer layer of the bi-layer balloon wall 24 may co-extruded during the manufacturing process of the balloon. Typical balloon materials may include polymer materials, some examples of which are listed herein.

Additionally, as illustrated in FIG. 1, the balloon 20 may include one, two, three, four, five, six or more reinforced portions circumferentially arranged around the longitudinal axis of the balloon 20. The balloon 20 illustrated in FIG. 1 includes three reinforced portions 22*a*, 22*b*, 22*c*. The reinforced portion 22*c* is hidden from view in FIG. 1, but shown in FIGS. 3-5.

In some examples, the reinforced portions 22*a*, 22*b*, 22*c* may include one or more interwoven (e.g., braided, woven, or knitted) filaments 34 attached to the outer surface of the balloon 20. The filaments 34 may be constructed from a variety of materials. For example, the filaments 34 may be constructed from silk, Kevlar®, or other suitable material. In other examples, the reinforced portions 22*a*, 22*b*, 22*c* may include a continuous, flexible strip of material attached to the balloon 20. Yet in other examples, the reinforced portions 22*a*, 22*b*, 22*c* may include polyimide strips, liquid crystal polymers or other similar materials.

In some examples, each of the reinforced portions 22*a*, 22*b*, 22*c* of FIG. 1 may each include one or more braided or interwoven filaments 34 disposed along an outer surface of balloon 20. In some examples, the filaments 34 may be braided, wound, wrapped, woven, etc. in a variety of configurations along each of the reinforced portions 22*a*, 22*b*, 22*c* of the balloon 20. For example, the filaments 34 may be extruded directly on to the outer surface of the balloon 20 in the configuration shown in FIG. 1. However, in other examples, the filaments 34 may be extruded with the balloon material such that the filaments 34 are partially embedded into the wall 24 of the balloon 20. In yet other examples, the filaments 34 may be extruded with the balloon material such that the filaments 34 are fully embedded into the wall 24 of the balloon 20. Alternatively, it can be appreciated that the filaments 34 may be adhesively bonded to an outer surface of the balloon 20. The adhesive may include thermoset adhesives that cure either via a chemical reaction or irradiation. In some examples, a polymer coating 26 (illustrated in FIG. 3) may be applied over the braided filaments 34. The polymer coating may encapsulate the braided filaments 34 along each of the reinforced portions 22*a*, 22*b*, 22*c*.

Figure 1A:
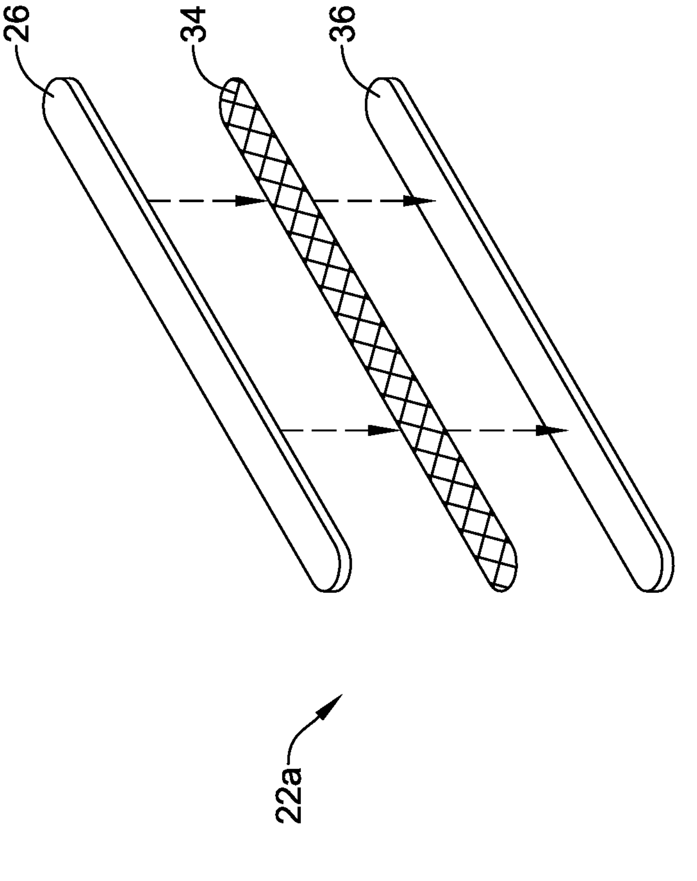
FIG. 1A illustrates an exploded view of a portion of an example medical balloon.

In other examples, each of the reinforced portions 22*a*, 22*b*, 22*c* may be constructed as a separate component, such as a textile strip, which is then attached to the outer surface of the balloon 20 in a subsequent manufacturing step. For example, FIG. 1A illustrates that the reinforced portions 22*a*, 22*b*, 22*c* may be formed as a pre-formed, separate component which includes a base material (e.g., polymer tie layer), the braided or interwoven filaments 34 and a top coating material 26 (e.g., a compliant polymer material). FIG. 1A illustrates that the separate component may be pre-formed to include the braided filaments 34 sandwiched between the base material 36 (e.g., polymer tie layer) and the polymer coating 26. Once the separate component is pre-formed, it may then be thermally bonded to the outer surface of the balloon 20 in a subsequent manufacturing step to the extrusion and blow molding of the balloon 20.

In some examples, the process of forming the separate component described with respect to FIG. 1A may include a lamination process. For example, the braided filaments 34 may be laminated between the base material (e.g., polymer tie layer) and the top coating material 26 (e.g., a compliant polymer material) to form the separate component which may then be attached to the outer surface of the balloon 20. In some instances, the separate component may be considered a textile strip, such as a laminated textile strip, for example.

It can be appreciated that the base layer 36 may be constructed from the same material as the material used to form the balloon 20 or a compatible material as the material used to form the balloon 20, thereby permitting the base layer 36 and the outer surface of the balloon 20 to melt (e.g., fuse, tie) together when heat welded. As used herein, thermal bonding refers to the melting of materials or a portion thereof by applying heat, laser, welding or some combination thereof, to obtain a mixing or bonding of the materials at the material interface.

Figure 2:
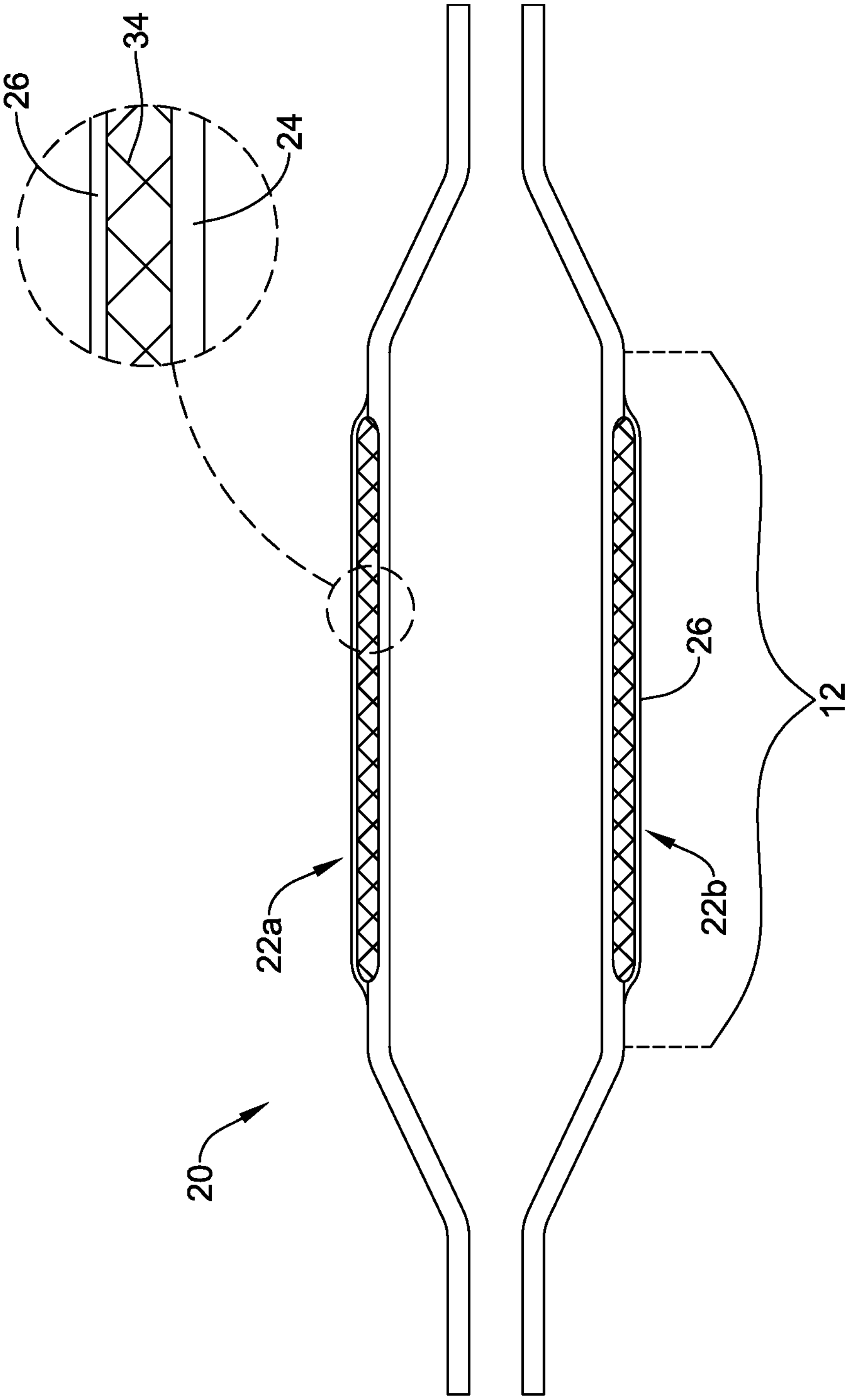
FIG. 2 is a cross-sectional view of the medical balloon of FIG. 1 taken along line 2-2 of FIG. 1.

FIG. 2 is a cross-sectional view of the balloon 20 taken along line 2-2 of FIG. 1. As described herein, FIG. 2 illustrates the reinforced portions 22*a*, 22*b* (reinforced portion 22*c* is hidden from view) extending longitudinally along the body portion 12 of the balloon 20. Further, the detailed view of FIG. 2 shows the filaments 34 disposed along the outer surface of the balloon wall 24. As discussed herein, the braided or interwoven filaments 34 may be disposed directly on the outer surface of the balloon wall 24 (e.g., the braided or interwoven filaments 34 may be extruded directly onto the outer surface of the balloon wall 24). However, in other examples, the filaments 34 may be partially or fully embedded into the balloon wall 24 (via an extrusion process or other suitable manufacturing method).

FIG. 2 further illustrates that the filaments 34 may be fully or partially covered by a polymer coating 26. In some examples, the polymer coating 26 may extend continuously (e.g., uninterrupted) along the entire length of the reinforced portions 22*a*, 22*b*, 22*c*, thereby fully encapsulating all of the braided or interwoven filaments 34 between the balloon wall 24 and the polymer coating 26.

Figure 3:
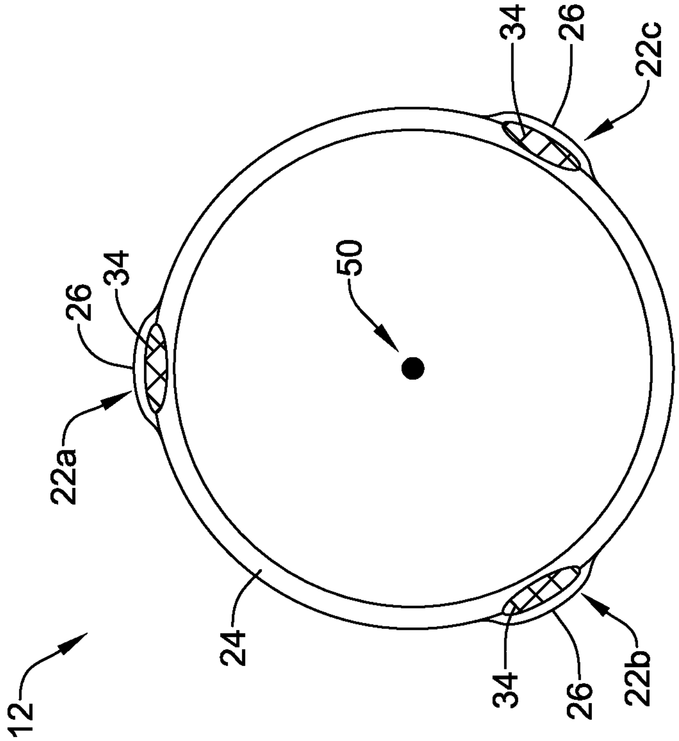
FIG. 3 is a cross-sectional view of the medical balloon of FIG. 1 taken along line 3-3 of FIG. 1.

FIG. 3 illustrates a cross-sectional view of the balloon 20 taken along line 3-3 of FIG. 1. FIG. 3 illustrates three reinforced portions 22*a*, 22*b*, 22*c* circumferentially arranged around the longitudinal axis 50 of the balloon 20. FIG. 3 illustrates that the three reinforced portions 22*a*, 22*b*, 22*c* may be equally spaced around the longitudinal axis 50 of the balloon 20. However, in other examples, the three reinforced portions 22*a*, 22*b*, 22*c* may be unequally spaced around the longitudinal axis 50 of the balloon 20. As discussed herein, the balloon 20 may include one, two, three, four, five, six or more reinforced portions (e.g., 22*a*, 22*b*, 22*c*) arranged around the longitudinal axis 50 of the balloon 20.

FIG. 3 further illustrates the braided or interwoven filaments 34 of each of the reinforced portions 22*a*, 22*b*, 22*c* disposed along the outer surface of the wall 24 of the balloon 20. As discussed herein, it can be appreciated from FIG. 3 that a circumferential portion of the balloon wall 24 extends between each of the reinforced portion 22*a*, 22*b*, 22*c*, thereby establishing discrete regions of continuous balloon wall 24 which is devoid of the filaments 34. Additionally, FIG. 3 illustrates that the filaments 34 of each reinforced portion 22*a*, 22*b*, 22*c* may include a polymer coating 26 disposed thereon. A discussed herein, the polymer coating 26 may fully encapsulate the filaments 34. In other words, FIG. 3 illustrates that the braided or interwoven filaments 34 of each reinforced portion 22*a*, 22*b*, 22*c* may be fully encapsulated between the polymer coating 26 and the balloon wall 24.

Figure 4:
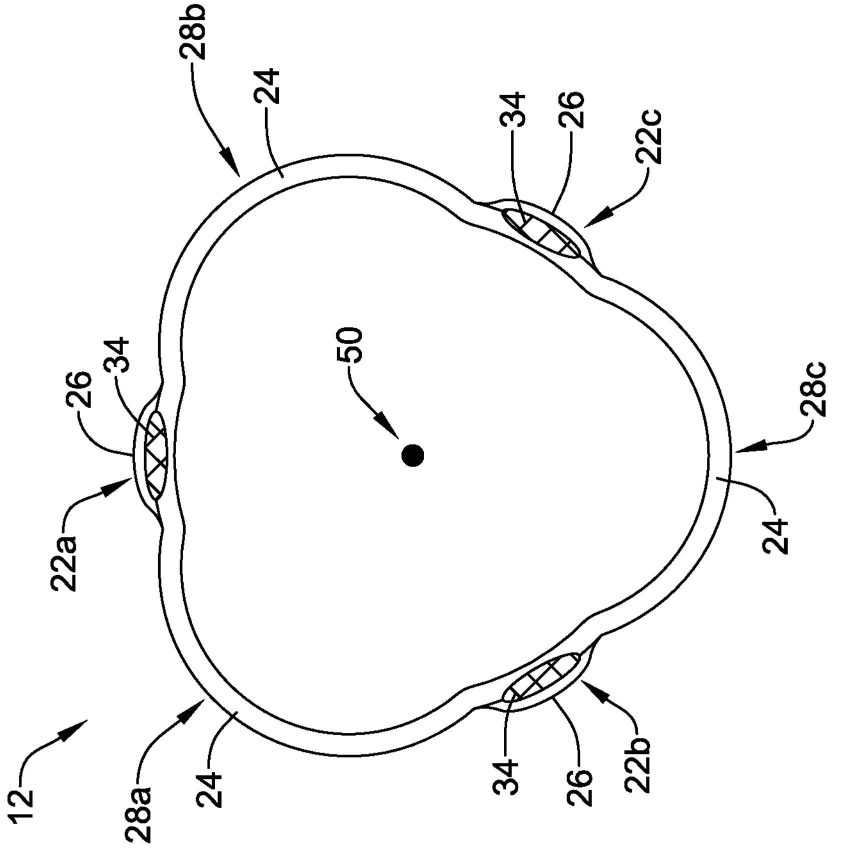
FIG. 4 is a cross-sectional view of the medical balloon of FIG. 1 in an expanded configuration.

FIG. 4 illustrates a cross-sectional view of the balloon 20 in an inflated configuration. It can be appreciated from FIG. 4 that as the balloon 20 is inflated, the portions 28*a*, 28*b*, 28*c* of the balloon wall 24 that are devoid of the filaments 34 (e.g., the portions of the balloon wall 24 extending between the reinforced portions 22*a*, 22*b*, 22*c*) may distend (e.g., stretch, expand, etc.) to a greater radial extent than the portions 22*a*, 22*b*, 22*c* of the balloon wall 24 which are reinforced/strengthened by the filaments 34. In other words, during inflation of the balloon 20, the reinforced portions 22*a*, 22*b*, 22*c*, may act to restrict the radial expansion of the portions 22*a*, 22*b*, 22*c* of the balloon wall 24 which are reinforced/strengthened by the braided or interwoven filaments 34, thereby permitting the portions 28*a*, 28*b*, 28*c* of the balloon wall 24 which are not reinforced/strengthened by the braided or interwoven filaments 34 to expand beyond the radial extent of the portions 22*a*, 22*b*, 22*c* of the balloon 20 which are reinforced/strengthened by the braided or interwoven filaments 34.

Figure 5:
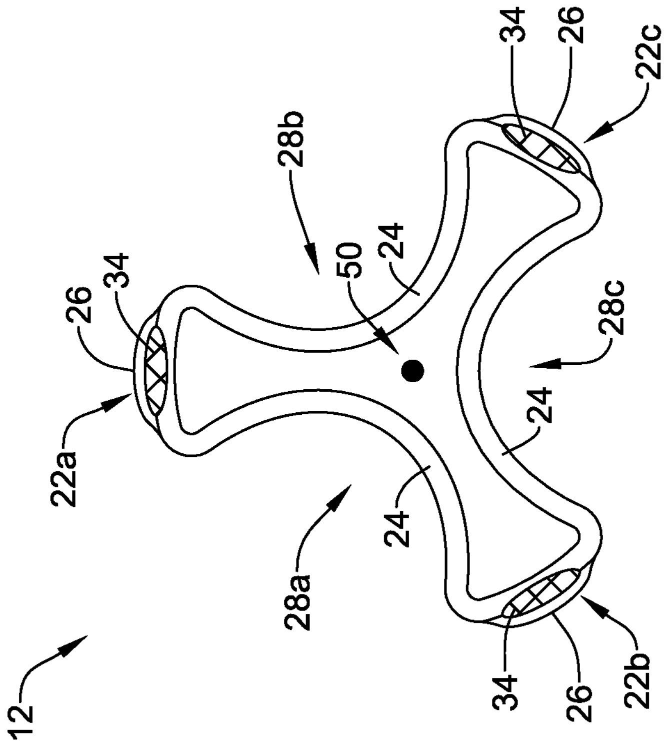
FIG. 5 is a cross-sectional view of the medical balloon of FIG. 1 in a deflated configuration.

FIG. 5 illustrates the illustrates a cross-sectional view of the balloon 20 in a deflated configuration. Following inflation of the balloon 20 (as illustrated in FIG. 4), the inflation media may be withdrawn through the outer shaft 30 which may generate a negative pressure (i.e., vacuum) that pulls the inner surface of balloon 20 radially inward toward the longitudinal axis 50. It can be appreciated that because the reinforced portions 22*a*, 22*b*, 22*c* are relatively stiff compared to the portions 28*a*, 28*b*, 28*c* of the balloon wall 24 extending between the reinforced portions 22*a*, 22*b*, 22*c* (e.g., the portions 28*a*, 28*b*, 28*c* of the balloon wall 24 which are devoid of the reinforcing/strengthening filaments 34), the portions 28*a*, 28*b*, 28*c* of the balloon wall extending between the reinforced portions 22*a*, 22*b*, 22*c* will more readily collapse inwardly towards the longitudinal axis 50 of the balloon. As shown in FIG. 5, the reinforced portions 22*a*, 22*b*, 22*c* are relatively stiff and, therefore, support the balloon wall 24 disposed therebetween. Thus, the circumferential portions 28*a*, 28*b*, 28*c* of the balloon wall 24 extending between the reinforced portions 22*a*, 22*b*, 22*c* may collapse more readily when the balloon 20 is deflated. It can be further appreciated that the resistance to collapse of the reinforced portions 22*a*, 22*b*, 22*c* of the balloon 20 compared to other portions of the balloon 20 may result in a symmetrical refolding of the balloon 20 during deflation. This symmetrical refolding of the balloon 20 may result in a smaller folded profile of the deflated balloon 20, which may enable the balloon to be more easily withdrawn into the guide catheter that was used for insertion of the balloon 20 into the body.

Figure 6:
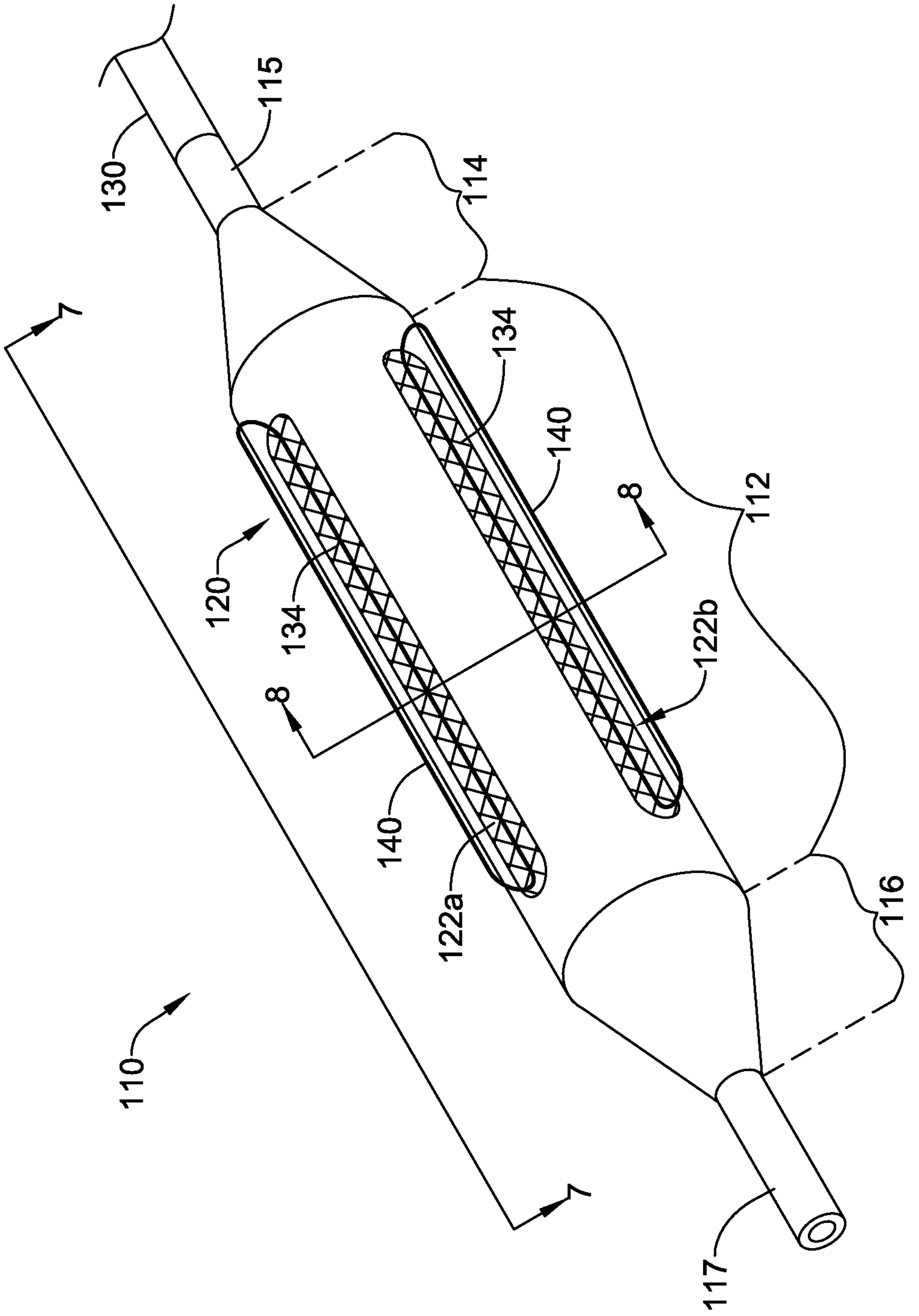
FIG. 6 is a perspective view of another medical balloon including a cutting member.

FIG. 6 illustrates another example balloon catheter 110. The example balloon 120 may be similar in form and function to the balloon catheter 10 discussed herein. The balloon catheter 110 may include an expandable medical balloon 120 mounted to a distal end of an outer shaft 130. The balloon 120 may be similar in form and function to the balloon 20 described herein. For example, the wall 124 (shown in the detailed view of FIG. 7) of the balloon 120 may include a bi-layer construction including an inner layer and an outer layer, whereby the inner layer is constructed of a lower durometer (e.g., softer) material as compared to the outer layer. It is contemplated that in other instances, the outer layer may be constructed of a lower durometer (e.g., softer) material as compared to the inner layer, if desired.

The medical balloon 120 may be designed to be utilized in a variety of medical procedures, including a valvuloplasty procedure. The outer shaft 130 may extend from a manifold assembly (not shown) positioned at a proximal end of the catheter shaft 130. The balloon 120 may further include a body portion 112, a proximal cone portion 114, a distal cone portion 116, a proximal waist portion 115, and a distal waist portion 117. The body portion 112 may be positioned between the proximal cone portion 114 and the distal cone portion 116, with the proximal waist portion 115 extending proximal of the proximal cone portion 114 and the distal waist portion 117 extending distal of the distal cone portion 116. The balloon 120 may be secured to the outer catheter shaft 30 at the proximal waist 115. It can be appreciated that an inner shaft (not shown) may extend within the outer catheter shaft 130, through the inner cavity of the balloon 120 and be secured to the distal waist 117. An inflation lumen may be defined within the space between the outer surface of the inner shaft and the inner surface of the outer shaft 130, similarly to that discussed with respect to the balloon catheter 10. The inflation lumen may be utilized to transport inflation media to and from the balloon 120.

Similarly, to those discussed with respect to the balloon 20, the balloon 120 illustrated in FIG. 6 may include one, two, three, four, five, six or more reinforced portions, whereby the reinforced portions are circumferentially arranged around the longitudinal axis of the balloon 120. For example, the balloon 120 illustrated in FIG. 6 includes three reinforced portions 122*a*, 122*b*, 122*c*, whereby the reinforced portion 122*c* is hidden from view in FIG. 6, but shown in FIG. 8.

Like the reinforced portions 22*a*, 22*b*, 22*c*, discussed herein, each of the reinforced portions 122*a*, 122*b*, 122*c* of the balloon 120 may include one or more interwoven (e.g., braided, woven, or knitted) filaments 134 disposed along the outer surface of the balloon 120. The filaments 134 may be constructed from a variety of materials. For example, the filaments 134 may be constructed from silk, Kevlar®, or other suitable material. Further, the braided or interwoven filaments 134 of each of the reinforced portions 122*a*, 122*b*, 122*c* may be disposed along the outer surface of the balloon 120 in a manner similar to that described with respect to the reinforced portions 22*a*, 22*b*, 22*c* of the balloon 20. Additionally, a polymer coating 126 (illustrated in FIGS. 7-8) may be applied over the filaments 134 of the reinforced portions 122*a*, 122*b*, 122*c* of the balloon 120.

FIG. 6 further illustrates that the medical balloon 120 may include a cutting member 140 coupled to each of the reinforced portions 122*a*, 122*b*, 122*c*. The cutting member 140 may be utilized to cut or score the tissue of a diseased heart valve during a valvuloplasty procedure. In some examples, the cutting members 140 may include an elongated filament, such as a wire or a fiber. The cutting member 140 may be formed from a variety of materials, including a polymer or a metal material. In some instances, the cutting member 140 may extend along and be attached to the balloon 120 via engagement with the interwoven filaments 134 of the reinforced portions 122*a*, 122*b*, 122*c*.

Figure 7:
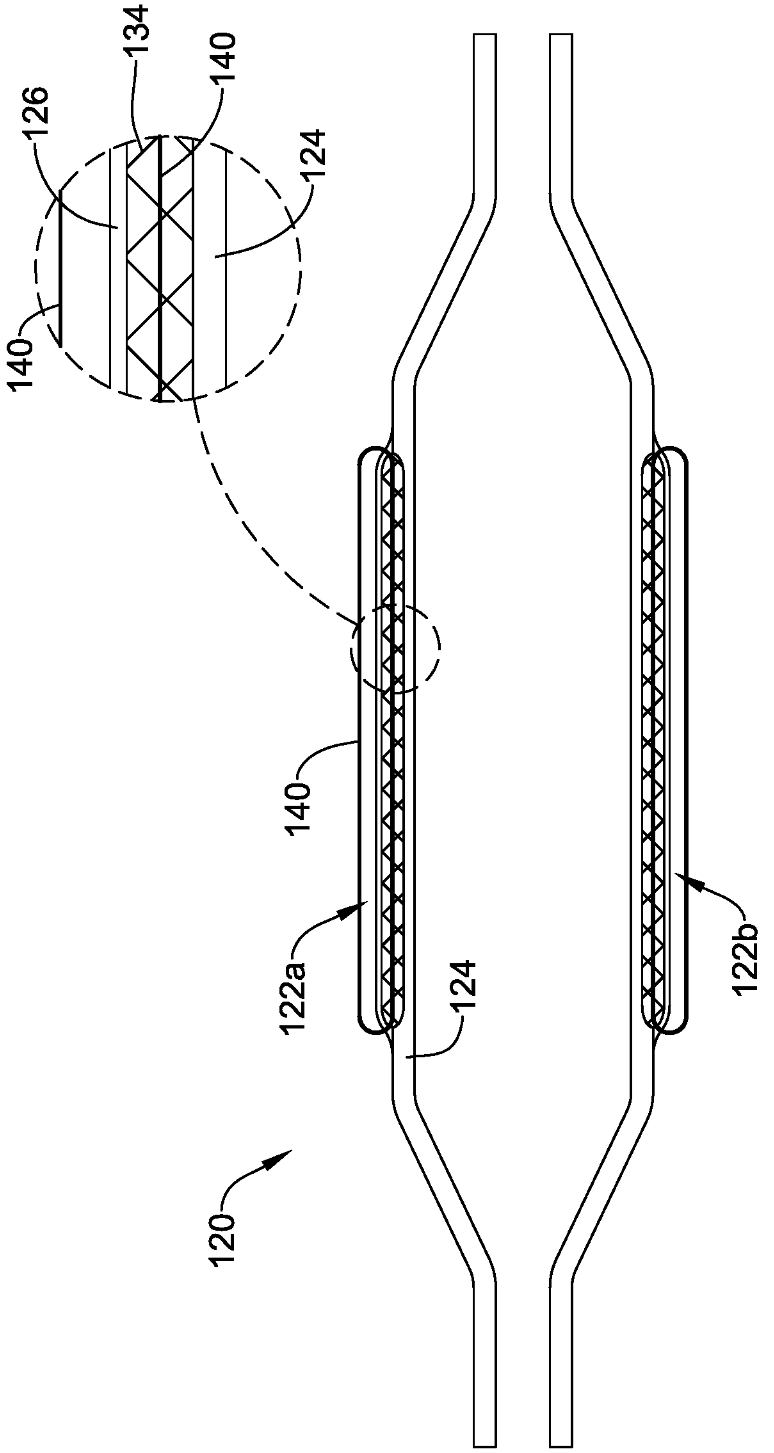
FIG. 7 is a cross-sectional view of the medical balloon of FIG. 1 taken along line 7-7 of FIG. 6.

FIG. 7 illustrates a cross-sectional view of the balloon 120 taken along line 7-7 of FIG. 6. FIG. 7 shows that each of the cutting members 140 of the reinforced portions 122*a*, 122*b*, 122*c* may form a complete longitudinally-extending loop, whereby a first portion of the cutting member 140 may pass through or under the interwoven filaments 134 of each reinforced portion 122*a*, 122*b*, 122*c*, respectively, while a second portion of the cutting member 140 is positioned radially outward of the reinforced portions 122*a*, 122*b*, 122*c*. In some instances, the first portion of the cutting member 140 may be interwoven through the filaments 134 of one of the reinforced portions 122*a*, 122*b*, 122*c*. It can be appreciated that the engagement of the cutting member 140 with the interwoven filaments 134 may anchor (e.g., fixedly attach) the cutting member 140 to each of the reinforced portions 122*a*, 122*b*, 122*c* of the balloon 120. For example, it can be appreciated that one or more of the filaments 134 may pass over and/or under the cutting member 140, thereby fixedly attaching the cutting member 140 to each of the reinforced portions 122*a*, 122*b*, 122*c* of the balloon 120.

Figure 8:
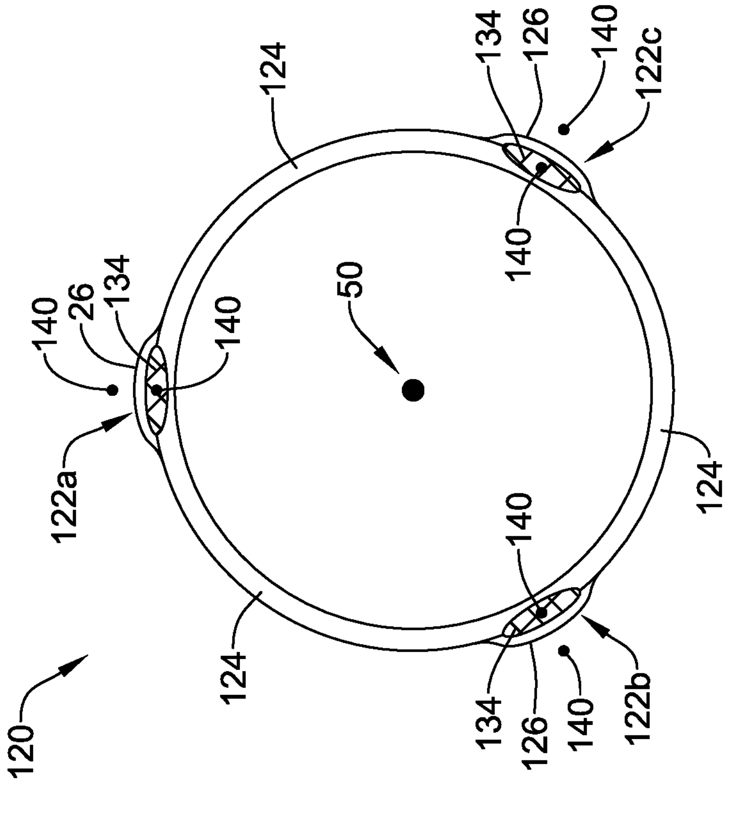
FIG. 8 is a cross-sectional view of the medical balloon of FIG. 6 taken along line 8-8 of FIG. 1.

FIG. 8 illustrates a cross-sectional view of the balloon 120 taken along line 8-8 of FIG. 6. FIG. 8 illustrates the three reinforced portions 122*a*, 122*b*, 122*c* circumferentially arranged around the longitudinal axis 50 of the balloon 120. FIG. 8 illustrates that the three reinforced portions 122*a*, 122*b*, 122*c* may be equally spaced around the longitudinal axis 50 of the balloon 120. However, in other examples, the three reinforced portions 122*a*, 122*b*, 122*c* may be unequally spaced around the longitudinal axis 50 of the balloon 120. As discussed herein, the balloon 120 may include one, two, three, four, five, six or more reinforced portions (e.g., 122*a*, 122*b*, 122*c*) arranged around the longitudinal axis 50 of the balloon 20.

FIG. 8 further illustrates the braided or interwoven filaments 134 of each of the reinforced portions 122*a*, 122*b*, 122*c* disposed along the outer surface of the wall 124 of the balloon 120. As discussed herein, it can be appreciated from FIG. 8 that a circumferential portion of the balloon wall 124 extends between each of the reinforced portion 122*a*, 122*b*, 122*c*, thereby establishing discrete regions of continuous balloon wall 124 which is devoid of the filaments 134. Additionally, FIG. 8 illustrates that the braided or interwoven filaments 134 of each reinforced portion 122*a*, 122*b*, 122*c* may include a polymer coating 126 disposed thereon. Accordingly, the polymer coating 126 may fully encapsulate the braided filaments 134 between the polymer coating 126 and the balloon wall 124. In other words, FIG. 8 illustrates that the braided filaments 134 of each reinforced portion 122*a*, 122*b*, 122*c* may be fully encapsulated between the polymer coating 126 and the balloon wall 124.

Additionally, FIG. 8 further illustrates a cutting element 140 fixedly attached to each of the reinforced portions 122*a*, 122*b*, 122*c*. As described herein, FIG. 8 further illustrates a portion of the cutting element 140 positioned within or under the interwoven filaments 134 of each of the reinforced portions 122*a*, 122*b*, 122*c*. As described herein, FIG. 8 illustrates that each of the cutting elements 140 may include a portion which is attached to the balloon 120 via individual filaments 134 passing over and/or under the cutting element 140, thereby fixedly attaching the cutting element 140 to each of the reinforced portions 122*a*, 122*b*, 122*c* of the balloon 120.

It can be further appreciated from FIG. 8 that a portion of the cutting element 140 may be spaced away from (e.g., radially outward of) the polymer coating 126 which may encapsulate both the braided or interwoven filaments 134 and the portion of the cutting element 140 which is attached to the braided or interwoven filaments 134. For example, it can be appreciated by referring back to FIG. 7 that the looped portion of the cutting element 140 which does not pass through or under the braided or interwoven filaments 134 of the reinforcing portions 122*a*, 122*b*, 122*c* may extend radially away from the filaments 134 and pass through the polymer coating 126 to complete the looped configuration of the cutting element 140 as shown in FIG. 7. Accordingly, referring back to the cross-section shown in FIG. 8, it can be appreciated that a portion of the cutting element 140 may be exposed exterior of and/or spaced radially away from the outer surface of the polymer coating 126 of each of the reinforced portions 122*a*, 122*b*, 122*c*.

Figure 9:
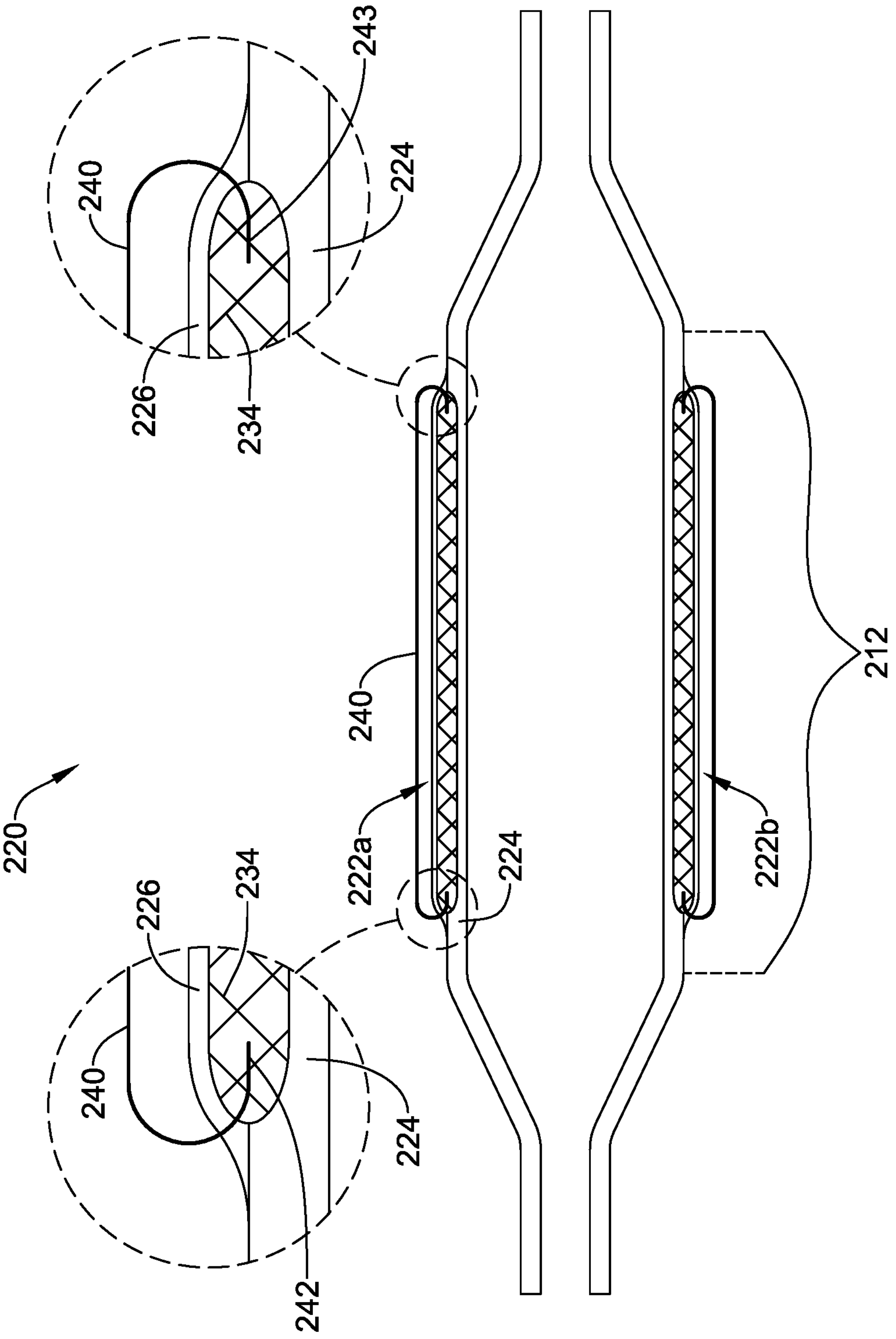
FIG. 9 is a cross-sectional view of another example medical balloon including a cutting member.

FIG. 9 illustrates a cross-sectional view of another example medical balloon 220. The balloon 220 shown in FIG. 9 may be similar in form and function to the balloon 120 of FIG. 7. For example, FIG. 9 illustrates the balloon 220 including a cutting element 240 attached to a reinforced portion 222*a*, which is similar to the attachment of the cutting element 140 to the reinforced portion 122*a* shown in FIG. 7. The cutting member 140 may be utilized to cut or score the tissue of a diseased heart valve during a valvuloplasty procedure. In some instances, the cutting member 140 may be an elongate filament, such as a wire or a fiber, if desired.

However, unlike FIG. 7, FIG. 9 illustrates that the cutting element 240 of the balloon 220 may not form a complete longitudinal loop along the length of the reinforced portion 222*a*. Rather, the detailed view of FIG. 9 illustrates that the cutting member 240 may include a first end portion 242 and a second end portion 243. Additionally, FIG. 9 illustrates that the first end portion 242 of the cutting element 240 may be attached to the braided or interwoven filaments 234 at a first end region of the balloon body 212 and the second end portion 243 of the cutting element 240 may be attached to the braided or interwoven filaments 234 at a second end region of the balloon body 212. In some instances, the first end portion 242 of the cutting element 240 may be embedded in the reinforced portion 222*a* and the second end portion 242 of the cutting element 240 may be embedded in the reinforced portion 222*a*, while a middle portion of the cutting member 240 is positioned radially outward of the reinforced portion 222*a*.

It can be appreciated that the first end portion 242 and the second end portion 243 of the cutting element 240 may be attached to the braided or interwoven filaments 234 in a similar manner to that described with respect to the attachment of the cutting element 140 with the braided or interwoven filaments 134 described above with respect to FIG. 7. For example, one or more of the filaments 234 may pass over and/or under both the first end portion 242 and the second end portion 243 of each of the cutting elements 240, thereby securing each of the cutting elements 240 to each of the reinforced portions 222*a*, 222*b*, 222*c* of the balloon 220. The detailed views of FIG. 9 further illustrate the polymer coating 226 encapsulating the filaments 234, the first end portion 242 of the cutting element 240 and second end portion 243 of the cutting element 240.

Figure 10:
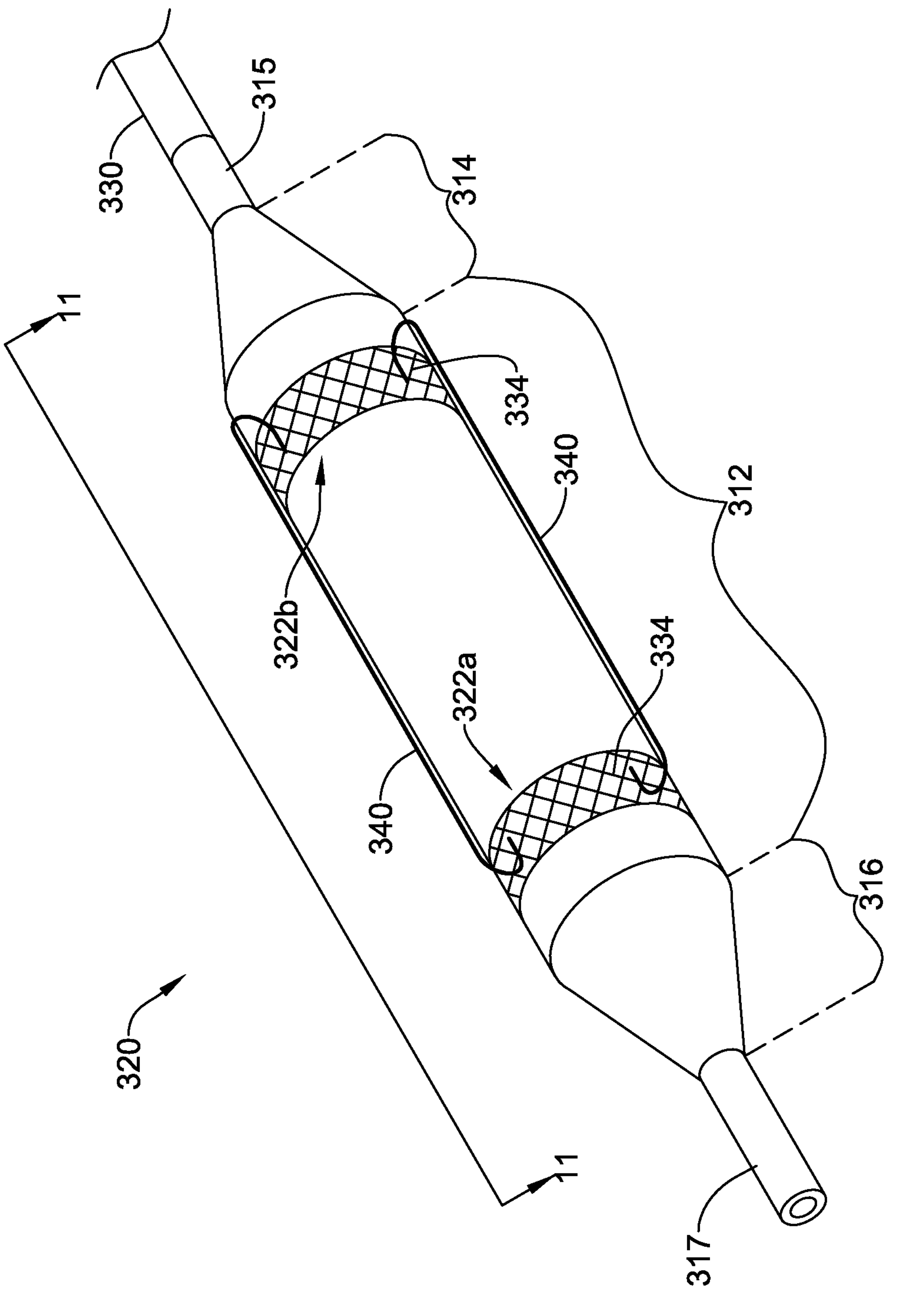
FIG. 10 is a perspective view of another example medical balloon including a cutting member.

FIG. 10 illustrates another example medical balloon 320. The balloon 320 shown in FIG. 10 may be similar in form and function to other medical balloons described herein. For example, the wall 324 (shown in the detailed view of FIG. 7) of the balloon 320 may include a bi-layer construction including an inner layer and an outer layer, whereby the inner layer is constructed of a lower durometer (e.g., softer) material as compared to the outer layer. It is contemplated that in other instances, the outer layer may be constructed of a lower durometer (e.g., softer) material as compared to the inner layer, if desired.

Further, an outer shaft 330 may extend from a manifold assembly (not shown) positioned at a proximal end of the outer shaft 330. The balloon 320 may include a body portion 312, a proximal cone portion 314, a distal cone portion 316, a proximal waist portion 315, and a distal waist portion 317. The balloon 320 may be secured to the outer catheter shaft 330 at the proximal waist 315. Further, it can be appreciated that an inner shaft (not shown) may extend within the outer catheter shaft 330, through the inner cavity of the balloon 320 and be secured to the distal waist 317. An inflation lumen may be defined within the space between the outer surface of the inner shaft and the inner surface of the outer shaft 330, similarly to that discussed with respect to the balloon catheter 10. The inflation lumen may be utilized to transport inflation media to and from the balloon 320.

Further, the balloon 320 of FIG. 10 may include a first reinforced portion **322*a* positioned along the distal end region of the body portion 312 and a second reinforced portion 322*b* positioned along the proximal end region of the body portion 312. Additionally, each of the first reinforced portion 322*a* and the second reinforced portion 322*b* may include a plurality of braided or interwoven filaments 334 which extend circumferentially around the outer surface of the balloon 320. The filaments 334 may be similar in form and function to other filaments disclosed herein. For example, the filaments 334 may be constructed from silk, Kevlar®, or other suitable material. Further, the braided or interwoven filaments 334 of each of the reinforced portions 322*a*, 322*b* may be disposed along the outer surface of the balloon 320 in a manner similarly to that described herein with respect to the reinforced portions 22*a*, 22*b*, 22*c* of the balloon 20. Additionally, a polymer coating 326 (show in the detailed view of FIG. 11) may be applied over the filaments 334 of the reinforced portions 322*a*, 322*b* of the balloon 320. FIG. 10 further illustrates that the balloon 320 may include one or more cutting members 340 attached to the reinforced portions 322*a*, 322*b*. The cutting members 340** may be utilized to cut or score the tissue of a diseased heart valve during a valvuloplasty procedure.

Figure 11:
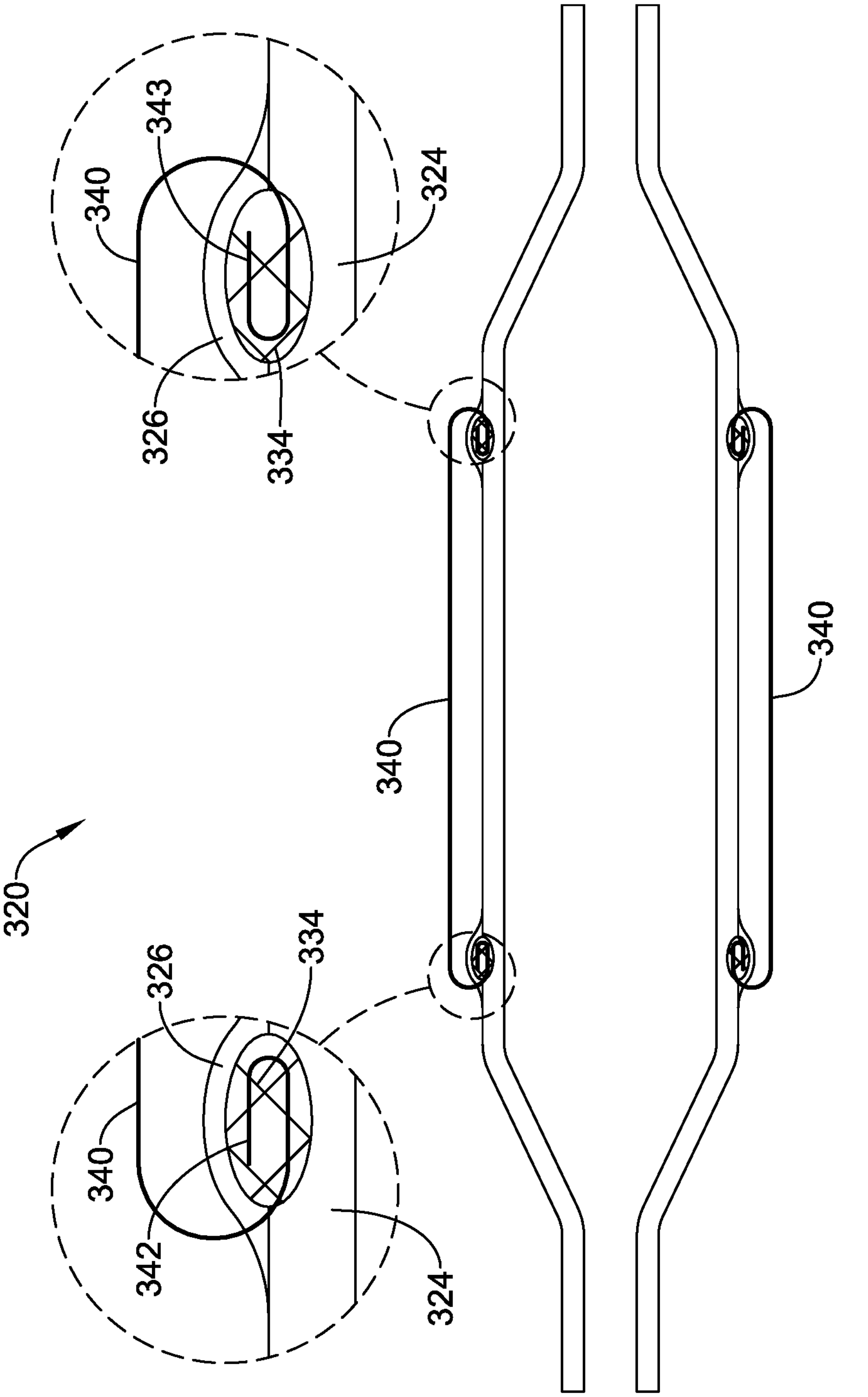
FIG. 11 is a cross-sectional view of the medical balloon of FIG. 10 taken along line 11-11 of FIG. 10.

FIG. 11 illustrates that the cutting members 340 may be similar in form and function to the cutting members 240 described with respect to FIG. 9. For example, the detailed views of FIG. 11 illustrate that the cutting members 340 may include a first end portion 342 and a second end portion 343. Additionally, FIG. 11 illustrates that the first end portion 342 of the cutting element 340 may be attached to the braided filaments 334 at the reinforced portion **322*a* and the second end portion 343 of the cutting element 340 may be attached to the braided filaments 334 at the reinforced portion 322*b*. It can be appreciated that the first end portion 342 and the second end portion 343 of the cutting element 340 may be attached to the braided or interwoven filaments 334 of each of the reinforced portion 322*a*, 322*b* in a similar manner to that described with respect to the attachment of the cutting element 240 with the braided or interwoven filaments 234 described above with respect to FIG. 9. For example, one or more of the filaments 334 may pass over and/or under both the first end region 342 and the second end region 343 of each of the cutting elements 340, thereby securing each of the cutting elements 340 to each of the reinforced portions 322*a*, 322*b* of the balloon 320. The detailed views of FIG. 11 further illustrate the polymer coating 326 encapsulating the filaments 334, the first end portion 342 of the cutting element 340 and second end portion 343 of the cutting element 340**.

It can be further appreciated from FIGS. 10-11 that while the first end portion 342 and the second end portion 343 of each of the cutting elements 340 are attached to the reinforced portions **322*a*, 322*b* of the balloon 320 (e.g., engaged with the braided fibers 334 and covered by the polymer coating 326), the remainder of each of the cutting elements 340 may remain unattached to the outer surface of the balloon 320 and extend outward thereof. For example, FIG. 11 illustrates that a portion of the cutting elements 340 may be spaced radially away from the outer surface of the balloon 320. In some instances, the first end portion 342 of the cutting element 340 may be embedded in the reinforced portion 322*a* and the second end portion 342 of the cutting element 340 may be embedded in the reinforced portion 322*a*, while a middle portion of the cutting member 340 is positioned radially outward of the reinforced portion 322*a***.

Figure 12:
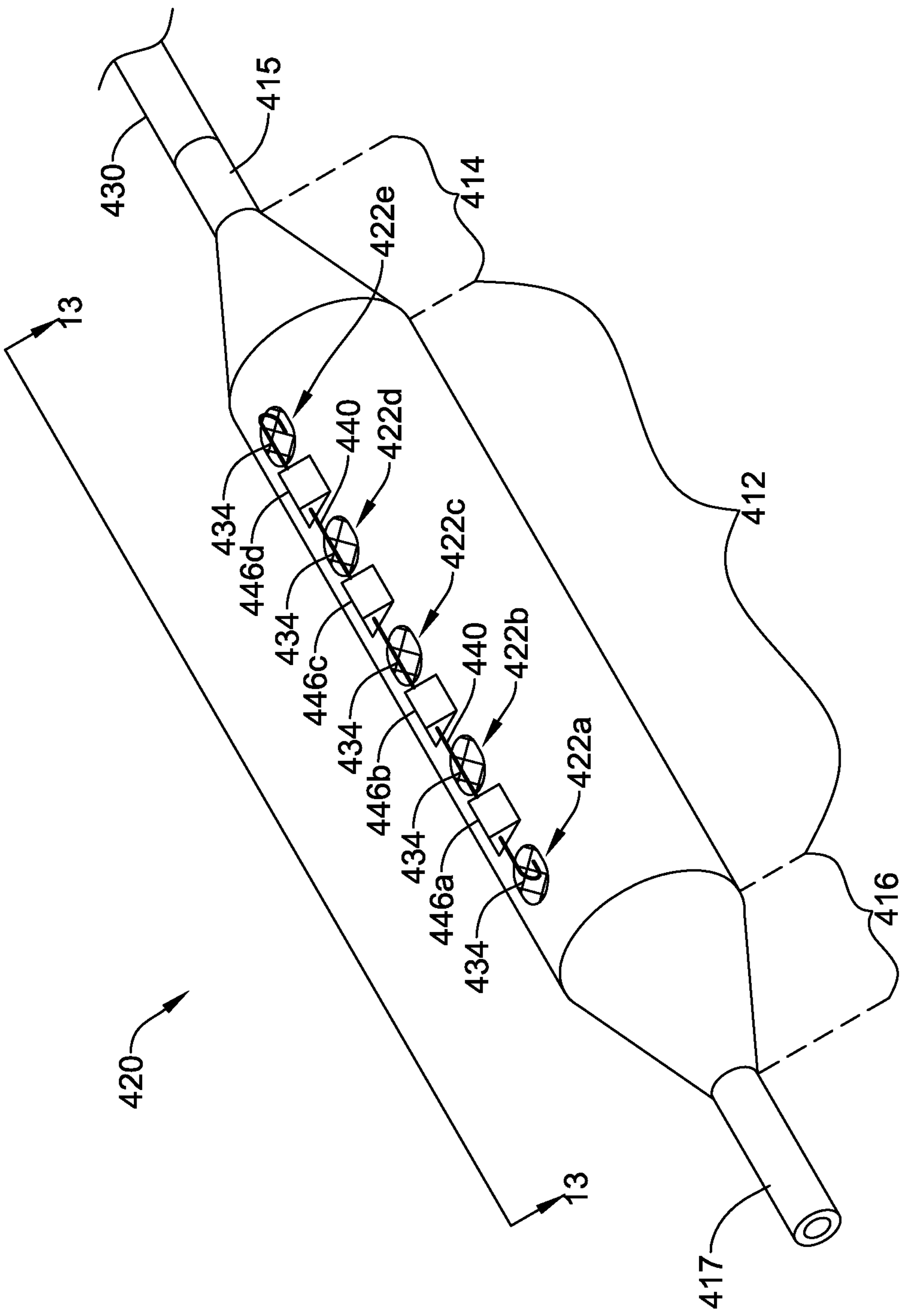
FIG. 12 is a perspective view of another example medical balloon including a plurality of cutting members.

FIG. 12 illustrates a perspective view of another example medical balloon 420. The balloon 420 shown in FIG. 12 may be similar in form and function to other medical balloons described herein. For example, the wall 424 (shown in the detailed view of FIG. 13) of the balloon 420 may include a bi-layer construction including an inner layer and an outer layer, whereby the inner layer is constructed of a lower durometer (e.g., softer) material as compared to the outer layer. It is contemplated that in other instances, the outer layer may be constructed of a lower durometer (e.g., softer) material as compared to the inner layer, if desired.

Further, an outer shaft 430 may extend from a manifold assembly (not shown) positioned at a proximal end of the outer shaft 430. The balloon 420 may include a body portion 412, a proximal cone portion 414, a distal cone portion 416, a proximal waist portion 415, and a distal waist portion 417. The balloon 420 may be secured to the outer catheter shaft 430 at the proximal waist 415. Further, it can be appreciated that an inner shaft (not shown) may extend within the outer catheter shaft 430, through the inner cavity of the balloon 420 and be secured to the distal waist 417. An inflation lumen may be defined within the space between the outer surface of the inner shaft and the inner surface of the outer shaft 430, similarly as that discussed with respect to the balloon catheter 10. The inflation lumen may be utilized to transport inflation media to and from the balloon 420.

FIG. 12 further illustrates that the balloon 420 may include one or more cutting members (e.g., blades, micro-surgical blades, artherotomes) **446*a*, 446*b*, 446*c*, 446*d* disposed along the outer surface of the balloon 420. The cutting members 446*a*, 446*b*, 446*c*, 446*d* may be formed from a variety of materials, including polymer materials (including those listed herein), metals, and combinations thereof. Further, each of the cutting members 446*a*, 446*b*, 446*c*, 446*d* may be segmented, whereby each blade includes one or more cut-outs and/or regions of increased flexibility along its length. It can be appreciated that the balloon 420 may be inflated to expand a stenotic heart valve during a balloon valvuloplasty procedure. In some instances, the cutting members 446***a*, 446*b*, 446*c*, 446*d* may be designed to score or cut a stenotic heart valve as a pre-dilation step of the balloon valvuloplasty procedure.

The cutting members 446*a*, 446*b*, 446*c*, 446*d* may vary in number, position, and arrangement about the balloon 420. For example, the balloon 420 may include one, two, three, four, five, six, or more cutting members 446*a*, 446*b*, 446*c*, 446*d* that are disposed at any position along the balloon 420 in a regular, irregular, or any other suitable pattern.

FIG. 12 illustrates that the cutting members 446*a*, 446*b*, 446*c*, 446*d* may be arranged in series along an outer surface of the balloon 420. In other words, FIG. 12 illustrates that the cutting members 446*a*, 446*b*, 446*c*, 446*d* may be longitudinally aligned along the outer surface of the balloon 420 in a spaced apart manner. It can be appreciated that the arrangement of the cutting members 446*a*, 446*b*, 446*c*, 446*d* shown in FIG. 12 may increase the flexibility of the balloon 420 by dividing what might otherwise be a single cutting member into multiple parts or segments. Thus, the segmented cutting members 446*a*, 446*b*, 446*c*, 446*d*, due to their shortened length, may be more amenable to the bending or flexing of the balloon 420. For example, increasing the flexibility of the balloon 420 may improve the ability of the balloon 420 to treat a variety of diseased heart valves, some of which may not be readily treatable by other, less flexible, cutting balloons. It can be appreciated that the precise arrangement of cutting members 446*a*, 446*b*, 446*c*, 446*d* may include arrangements other than the arrangement shown in FIG. 12. For example, the cutting members 446*a*, 446*b*, 446*c*, 446*d* may have an arrangement whereby one or more of the cutting members 446*a*, 446*b*, 446*c*, 446*d* are longitudinally and/or radially offset to one another.

Figure 13:
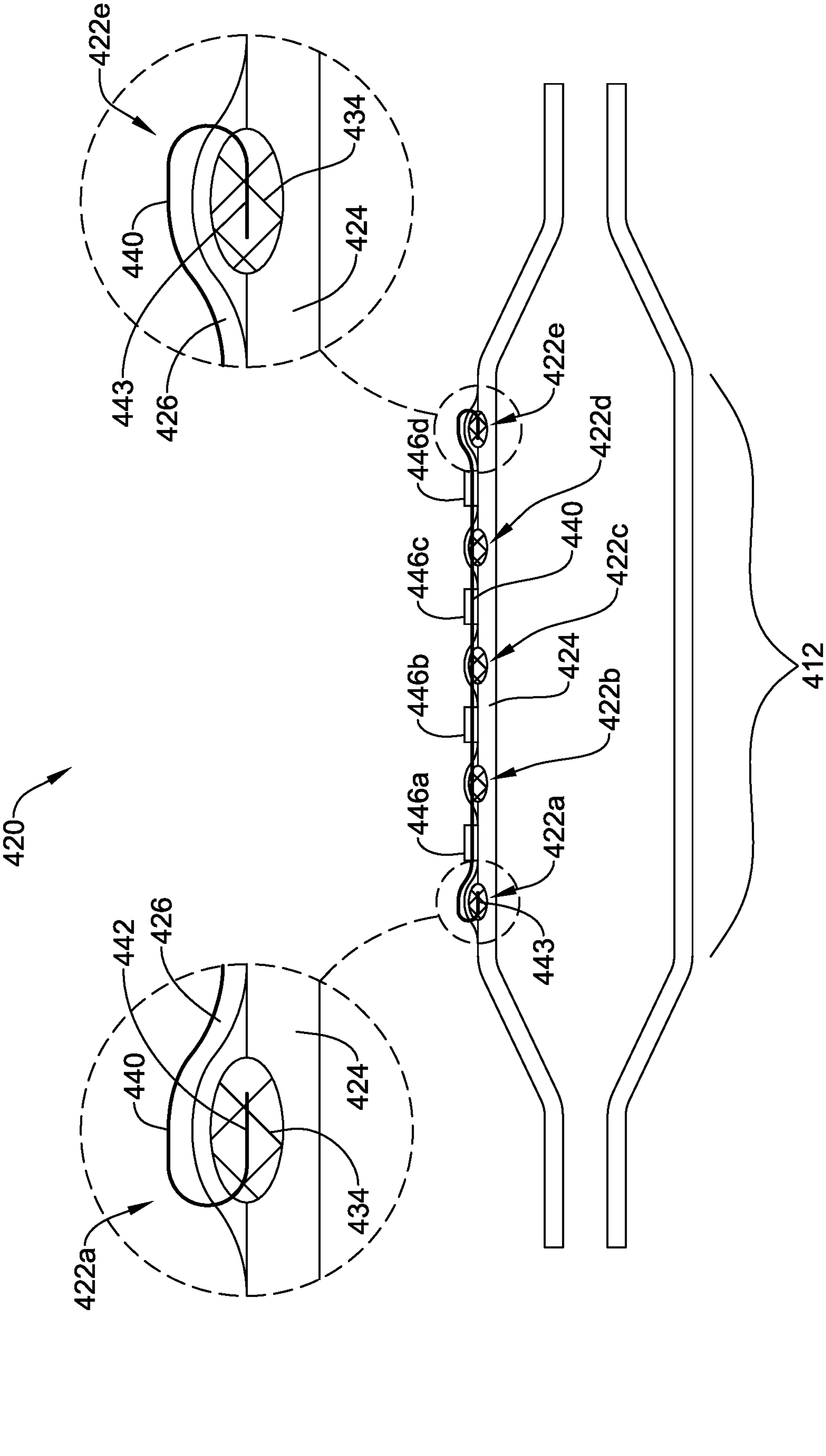
FIG. 13 is a cross-sectional view of the medical balloon of FIG. 12 taken along line 13-13 of FIG. 12.
Figure 14:
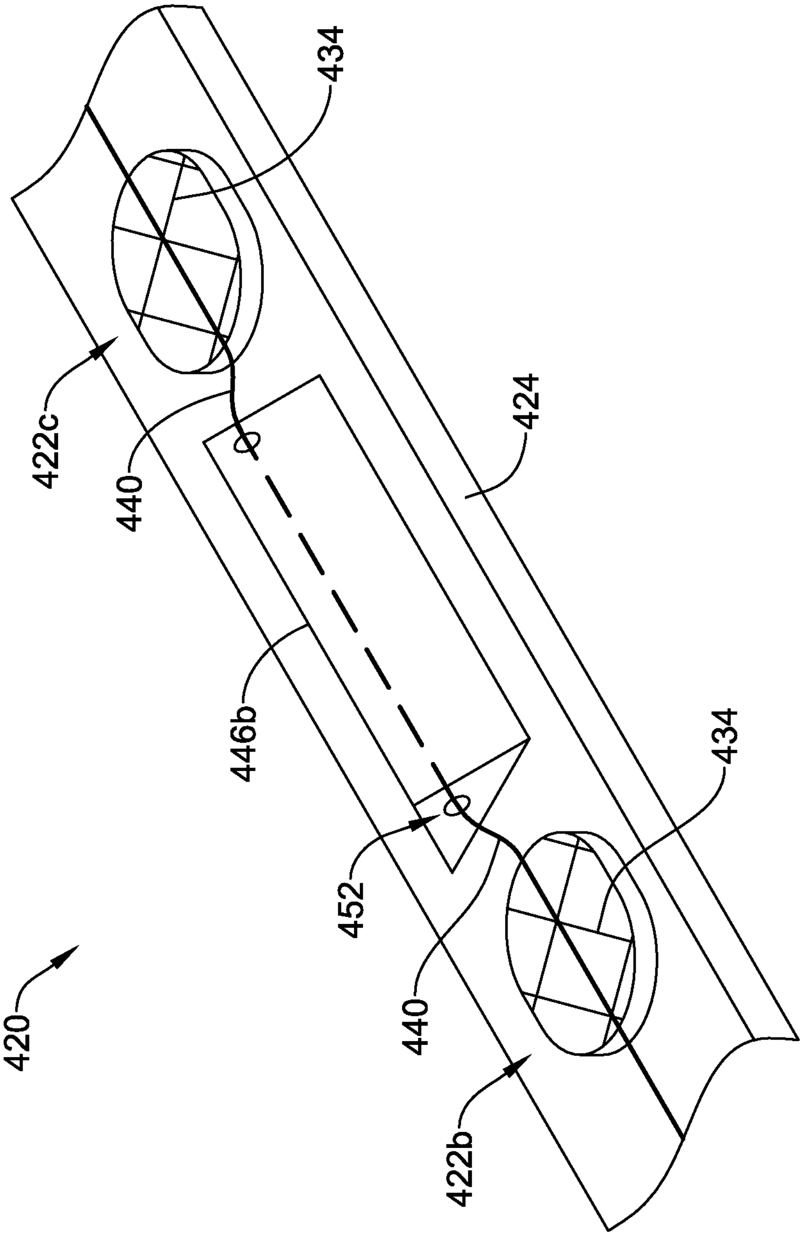
FIG. 14 illustrates a portion of the medical balloon shown in FIGS. 12-13.

As will be further discussed with respect to FIGS. 13-14, each of the cutting members 446*a*, 446*b*, 446*c*, 446*d* may be secured to the outer surface of the balloon 420 by a securement member 440. The securement member 440 may include a wire, cable, fiber, strip, etc. The securement member 440 may include a first end attached along a distal end region of the balloon 420 and second end attached along a proximal end region of the balloon 420.

Additionally, FIG. 12 illustrates that the securement member 440 may pass through the body of each of the cutting members 446*a*, 446*b*, 446*c*, 446*d*, and may be secured to the balloon 420 along multiple securement regions 422*a*, 422*b*, 422*c*, 422*d*, 422*e* located in the spaces/gaps between adjacent cutting members 446*a*, 446*b*, 446*c*, 446*d*. Thus, in some instances, the securement regions may alternate with the cutting members along the length of the balloon 420. A detailed explanation of the cutting members 446*a*, 446*b*, 446*c*, 446*d*, securement member 440, and the securement regions 422*a*, 422*b*, 422*c*, 422*d*, 422*e* is set forth below.

FIG. 13 illustrates a cross-sectional view of the balloon 420 taken along line 13-13 of FIG. 12. Similar to the attachment method described with respect to FIG. 11, the detailed views of FIG. 13 illustrate that the securement member 440 may include a first end portion 442 and a second end portion 443. Additionally, FIG. 13 illustrates that the first end portion 442 of the securement member 440 may be attached to a plurality of braided or interwoven filaments 434 of the securement region 422*a* and the second end portion 443 of the securement member 440 may be attached to a plurality of braided or interwoven filaments 434 of the securement region 422*e*.

As discussed herein, it can be further appreciated that the filaments 434 of each of the securement regions 422*a*, 422*b*, 422*c*, 422*d*, 422*e* shown in FIG. 13 may be similar in form and function to other filaments disclosed herein. For example, the filaments 434 may be constructed from silk, Kevlar®, or other suitable material. Further, the interwoven filaments 434 of each of the securement portions 422*a*, 422*b*, 422*c*, 422*d*, 422*e* shown in FIG. 13 may be disposed on the outer surface of the balloon 420 in a manner similar to that described herein with respect to the reinforced portions 22*a*, 22*b* of the balloon 20 described herein. Additionally, as illustrated in the detailed views of FIG. 13, a polymer coating 426 may be applied over the braided or interwoven filaments 434 of each of the securement regions 422*a*, 422*b*, 422*c*, 422*d*, 422*e* of the balloon 420.

As discussed herein, FIGS. 13-14 illustrate that the securement member 440 may pass through the body each of the cutting members 446*a*, 446*b*, 446*c*, 446*d* and may be secured to the balloon 420 along the securement regions 422*a*, 422*b*, 422*c*, 422*d*, 422*e* located in the spaces/gaps between adjacent cutting members. For example, FIG. 14 illustrates the securement member 440 extending through an aperture 452 of the cutting member 446*b*. It can be appreciated that the aperture 452 may extend along a longitudinal extent of the cutting member 446*b* from the distal end of the cutting member 446*b* to the proximal end of the cutting member 446*b*. Additionally, FIG. 14 illustrates that the securement member 440 may be attached to the balloon 420 at the securement region 422*b* (located distal to the cutting member 446*b*) and also at the securement region 422*c* (located proximal to the cutting member 446*b*). It can be appreciated that the securement member 440 may be designed to exert a radially downward force on cutting member 446*b*, thereby securing the cutting member 446*b* along the outer surface of the balloon 420.

It can be appreciated that the securement member 440 may be attached to the balloon 420 at each of the securement regions 422*a*, 422*b*, 422*c*, 422*d*, 422*e* via engagement with the braided or interwoven filaments 434 of each of securement regions 422*a*, 422*b*, 422*c*, 422*d*, 422*e*. The securement member 440 may engage the braided or interwoven filaments 434 in a similar manner to that described with respect to the attachment of other cutting elements with braided or interwoven filaments described herein. For example, at each of the securement regions 422*a*, 422*b*, 422*c*, 422*d*, 422*e*, one or more of the filaments 434 may pass over and/or under the securement member 440, thereby attaching the securement member 440 to the balloon 420 at each of the securement regions 422*a*, 422*b*, 422*c*, 422*d*, 422*e*. As discussed herein, a polymer coating 426 may encapsulate the braided or interwoven fibers 434 and the portion of the cutting element 440 extending along each of the securement regions 422*a*, 422*b*, 422*c*, 422*d*, 422*e*.

Additionally, it can be appreciated that, in some alternative examples, one or more of the cutting elements 140, 240, 340 of the balloons 120, 220, 320 may include an RF ablation wire. For example, the cutting elements 140, 240, 340 may be electrically coupled to an energy source located outside of a patient. Further, the cutting elements 140, 240, 340 of the balloons 120, 220, 320 may include one or more electrodes designed to delivery energy (e.g., radiofrequency energy) to ablate a target tissue site.

Additionally, it can be appreciated that, in some other alternative examples, the balloon catheters disclosed herein may include one or more components which may be utilized with cryotherapy treatments. For example, one or more of the balloons 120, 220, 320 disclosed herein may be designed to be inflated with a cooling fluid (i.e., coolant). Further, inflating and cooling the balloons 120, 220, 320 with a cooling fluid (i.e., coolant) may result in the formation of selectively hardened portions along the balloons 120, 220, 320 and/or a hardening of the cutting elements 140, 240, 340 attached to the balloons 120, 220, 320. The hardened portions may increase the amount of dilation force which can be generated by the balloons 120, 220, 320 and/or cutting elements 140, 240, 340 during the expansion of the balloons 120, 220, 320. An increased dilation force may permit the balloons 120, 220, 320 to effectively expand or score a diseased heart valve. Example polymers utilized to manufacture the medical balloons 20, 120, 220, 320, 420 and the various components of the balloons 20, 120, 220, 320, 420 disclosed herein include polymers such as polyethylene terephthalate (PET), polyetherimide (PEI), polyethylene (PE), etc. Some other examples of suitable polymers, including lubricious polymers, may include polytetrafluoroethylene (PTFE), ethylene tetrafluoroethylene (ETFE), fluorinated ethylene propylene (FEP), polyoxymethylene (POM), polybutylene terephthalate (PBT), polyether block ester, polyurethane, polypropylene (PP), polyvinylchloride (PVC), polyether-ester (for example, a polyether-ester elastomer such as ARNITEL® available from DSM Engineering Plastics), polyester (for example, a polyester elastomer such as HYTREL® available from DuPont), polyamide (for example, DURETHAN® available from Bayer or CRISTAMID® available from Elf Atochem), elastomeric polyamides, block polyamide/ethers, polyether block amide (PEBA, for example, available under the trade name PEBAX®), silicones, Marlex® high-density polyethylene, Marlex® low-density polyethylene, linear low density polyethylene (for example, REXELL®), polyetheretherketone (PEEK), polyimide (PI), polyphenylene sulfide (PPS), polyphenylene oxide (PPO), polysulfone, nylon, perfluoro(propyl vinyl ether) (PFA), other suitable materials, or mixtures, combinations, copolymers thereof, polymer/metal composites, and the like. In some embodiments, it may be desirable to use high modulus or generally stiffer materials so as to reduce balloon elongation. The above list of materials includes some examples of higher modulus materials. Some other examples of stiffer materials include polymers blended with liquid crystal polymer (LCP) as well as the materials listed above. For example, the mixture can contain up to about 5% LCP.

It should be understood that this disclosure is, in many respects, only illustrative. Changes may be made in details, particularly in matters of shape, size, and arrangement of steps without exceeding the scope of the disclosure. The disclosure's scope is, of course, defined in the language in which the appended claims are expressed.

What is claimed is:

1. A medical device, comprising:
an elongate shaft having a distal end region;
a balloon coupled to the distal end region, the balloon including a wall, a distal waist, a proximal waist and body portion positioned between the distal waist and the proximal waist;
a first reinforced region positioned along the body portion, the first reinforced region including a first plurality of filaments; and
a second reinforced region positioned along the body portion, the second reinforced region including a second plurality of filaments;
wherein the first reinforced region is circumferentially spaced from the second reinforced region such that the balloon wall extending between the first and the second reinforced regions is devoid of a filament; and
wherein the first plurality of filaments are arranged into a first strip of braided filaments extending along the body portion, and wherein the second plurality of filaments are arranged into a second strip of braided filaments extending along the body portion.

2. The medical device of claim 1, wherein the balloon wall extending between the first and second reinforced regions includes a first elasticity and wherein the first and the second reinforced regions include a second elasticity less than the first elasticity.

3. The medical device of claim 1, wherein the balloon is configured to be inflated to a first pressure, and wherein the balloon wall devoid of a filament has a diameter at the first pressure and wherein the first reinforced region has a diameter at the first pressure, and wherein the diameter of the balloon wall devoid of a filament is greater than the diameter of the first reinforced region at the first pressure.

4. The medical device of claim 1, wherein the first plurality of filaments are arranged in a braided configuration, and wherein the second plurality of filaments are arranged in a braided configuration.

5. The medical device of claim 1, wherein each of the first plurality of filaments and the second plurality of filaments include a wire.

6. The medical device of claim 1, wherein each of the first plurality of filaments and the second plurality of filaments include a fiber.

7. The medical device of claim 1, wherein the balloon wall includes an inner layer have a first durometer and an outer layer having a second durometer greater than the first durometer.

8. A medical device, comprising:
an elongate shaft having a distal end region;
a balloon coupled to the distal end region, the balloon including a wall, a distal waist, a proximal waist and body portion positioned between the distal waist and the proximal waist;
a first reinforced region positioned along the body portion, the first reinforced region including a first plurality of filaments; and
a second reinforced region positioned along the body portion, the second reinforced region including a second plurality of filaments;
wherein the first reinforced region is circumferentially spaced from the second reinforced region such that the balloon wall extending between the first and the second reinforced regions is devoid of a filament; and
wherein the first reinforced region includes a reinforced assembly, the reinforced assembly including:
a base material;
a plurality of filaments attached to the base material; and
a polymer coating attached to the plurality of filaments;
wherein the reinforced assembly is configured to be separately attached to an outer surface of the body portion.

9. A medical device, comprising:
an elongate shaft having a distal end region;
a balloon coupled to the distal end region, the balloon including a wall, a distal waist, a proximal waist and body portion positioned between the distal waist and the proximal waist;
a first reinforced region positioned along the body portion, the first reinforced region including a first plurality of filaments; and
a second reinforced region positioned along the body portion, the second reinforced region including a second plurality of filaments;
wherein the first reinforced region is circumferentially spaced from the second reinforced region such that the balloon wall extending between the first and the second reinforced regions is devoid of a filament; and wherein the first reinforced region further includes a polymer coating disposed along the first plurality of filaments.

10. A medical device, comprising:

an elongate shaft having a distal end region;

a balloon coupled to the distal end region, the balloon including a wall, a distal waist, a proximal waist and body portion positioned between the distal waist and the proximal waist;

a first reinforced region positioned along the body portion, the first reinforced region including a first plurality of filaments; and a second reinforced region positioned along the body portion, the second reinforced region including a second plurality of filaments;

wherein the first reinforced region is circumferentially spaced from the second reinforced region such that the balloon wall extending between the first and the second reinforced regions is devoid of a filament; and wherein the first reinforced region further includes a cutting member attached thereto.

11. The medical device of claim 10, wherein the cutting member includes a wire having a first region and a second region, and wherein the first region is configured to be attached to the plurality of filaments, and wherein the second region is configured to extend radially away from the first region.

12. The medical device of claim 11, wherein one or more of the plurality of filaments engage a portion of the first region of the wire.

13. The medical device of claim 10, wherein the cutting member includes an atherotome.

14. A balloon catheter, comprising:

an elongate shaft having a distal end region; and a balloon coupled to the distal end region, the balloon including a wall and a plurality of reinforced regions extending longitudinally along a cylindrical body portion of the balloon;

wherein each of the plurality of reinforced regions includes a mesh material;

wherein each of the plurality of reinforced regions is circumferentially spaced away from one another such that the portion of the balloon wall positioned between any two reinforced regions is devoid of a filament; and wherein at least one of the plurality of reinforced regions further includes a cutting member attached thereto.

15. The medical device of claim 14, wherein the portion of the balloon wall extending between any two reinforced regions includes a first elasticity and wherein each of the plurality of reinforced regions includes a second elasticity less than the first elasticity.

16. The medical device of claim 14, wherein the mesh material includes a plurality of fibers.

17. A balloon catheter, comprising:

an elongate shaft having a distal end region; and a balloon coupled to the distal end region, the balloon including a wall and a plurality of reinforced regions extending longitudinally along a cylindrical body portion of the balloon;

wherein each of the plurality of reinforced regions includes a mesh material;

wherein each of the plurality of reinforced regions is circumferentially spaced away from one another such that the portion of the balloon wall positioned between any two reinforced regions is devoid of a filament; and wherein the mesh material includes a plurality of wires.

* * * * *